United States Patent
Wallace et al.

(10) Patent No.: US 8,172,747 B2
(45) Date of Patent: May 8, 2012

(54) BALLOON VISUALIZATION FOR TRAVERSING A TISSUE WALL

(75) Inventors: Daniel T. Wallace, Burlingame, CA (US); Daniel T. Adams, Palo Alto, CA (US); Frederic H. Moll, Woodside, CA (US)

(73) Assignee: Hansen Medical, Inc., Mountain View, CA (US)

( * ) Notice: Subject to any disclaimer, the term of this patent is extended or adjusted under 35 U.S.C. 154(b) by 527 days.

(21) Appl. No.: 10/949,032

(22) Filed: Sep. 24, 2004

(65) Prior Publication Data

US 2005/0197530 A1 Sep. 8, 2005

Related U.S. Application Data

(60) Provisional application No. 60/506,293, filed on Sep. 25, 2003.

(51) Int. Cl.
*A61B 6/00* (2006.01)

(52) U.S. Cl. ........ 600/116; 600/101; 600/118; 600/476; 600/478

(58) Field of Classification Search ................. 600/433, 600/434, 115, 117, 122, 124, 207, 476, 478
See application file for complete search history.

(56) References Cited

U.S. PATENT DOCUMENTS

| | | | |
|---|---|---|---|
| 4,961,738 A | 10/1990 | Mackin | |
| 4,976,710 A | 12/1990 | Mackin | |
| 5,312,341 A * | 5/1994 | Turi | 604/103.05 |
| RE35,312 E * | 8/1996 | Christoudias | 600/207 |
| 5,725,523 A | 3/1998 | Mueller | |
| 5,766,163 A * | 6/1998 | Mueller et al. | 606/7 |
| 5,800,342 A * | 9/1998 | Lee et al. | 600/114 |
| 6,071,279 A * | 6/2000 | Whayne et al. | 606/41 |
| 6,190,353 B1 * | 2/2001 | Makower et al. | 604/95.01 |
| 6,201,989 B1 * | 3/2001 | Whitehead et al. | 600/476 |
| 6,692,430 B2 * | 2/2004 | Adler | 600/109 |
| 6,726,677 B1 * | 4/2004 | Flaherty et al. | 604/528 |
| 7,022,131 B1 * | 4/2006 | Derowe et al. | 623/1.11 |
| 2002/0068930 A1 * | 6/2002 | Tasto et al. | 606/32 |
| 2003/0181901 A1 * | 9/2003 | Maguire et al. | 606/41 |
| 2004/0097788 A1 * | 5/2004 | Mourlas et al. | 600/116 |
| 2005/0197530 A1 | 9/2005 | Wallace et al. | |

* cited by examiner

*Primary Examiner* — Long V. Le
*Assistant Examiner* — Ellsworth Weatherby
(74) *Attorney, Agent, or Firm* — Levine Bagade Han LLP

(57) ABSTRACT

Systems and methods for controllably traversing a tissue wall. In one embodiment, a distal end of a catheter is positioned and/or repositioned utilizing direct visualization out the distal end of the catheter, as facilitated by an imaging element disposed within the distal tip of the catheter. An inflatable balloon may comprise a portion of the distal tip of the catheter for structural and/or visualization media purposes. A tissue traversing element may be forwarded through a working lumen defined by the catheter and controllably pushed through a tissue wall as observed with the imaging element. The tissue traversing element may comprise sensors and the like to facilitate monitoring of changes in pressure, color, oxygen saturation, flow rate, and echo timing, to determine the position of the tissue traversing member relative to the tissue wall.

23 Claims, 22 Drawing Sheets

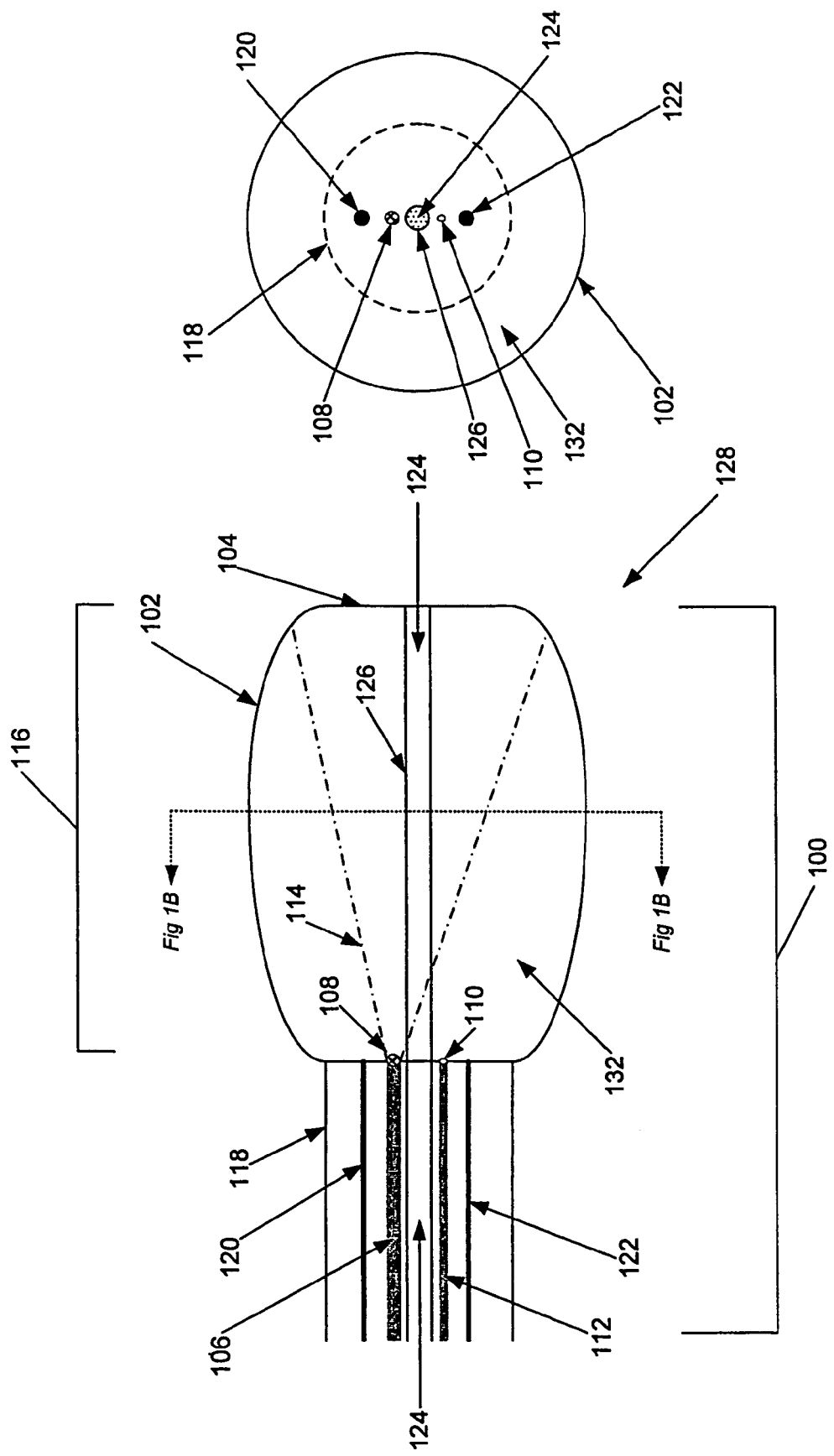

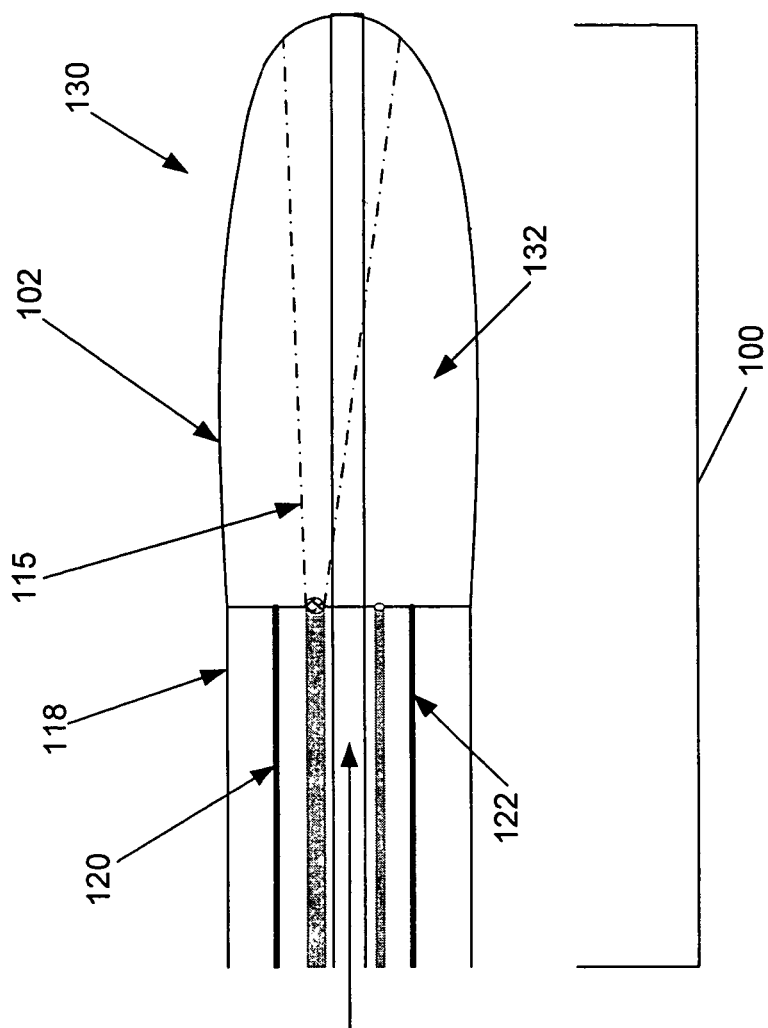
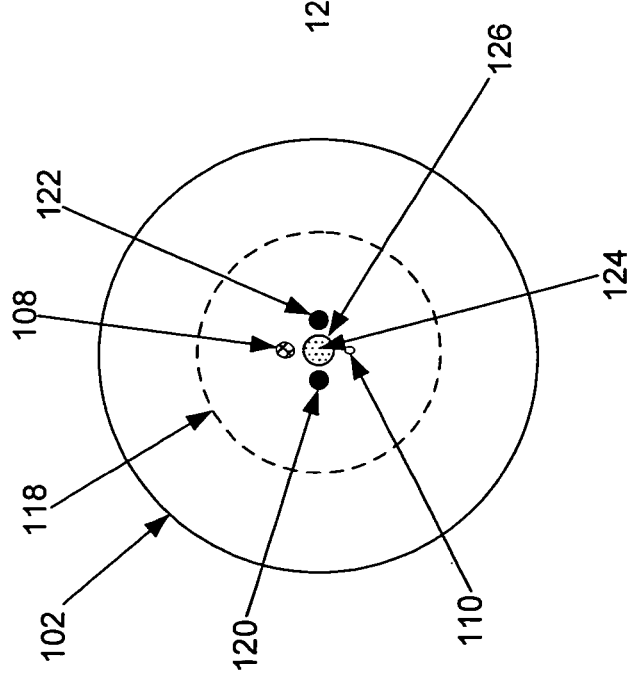
Figure 1D
Figure 1C

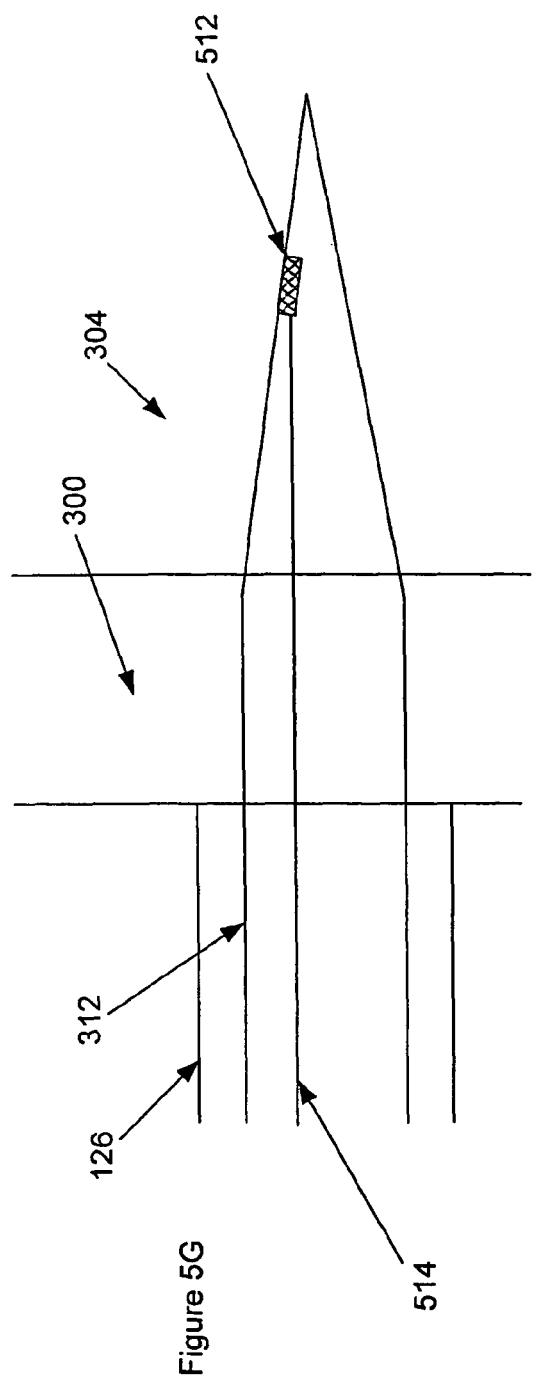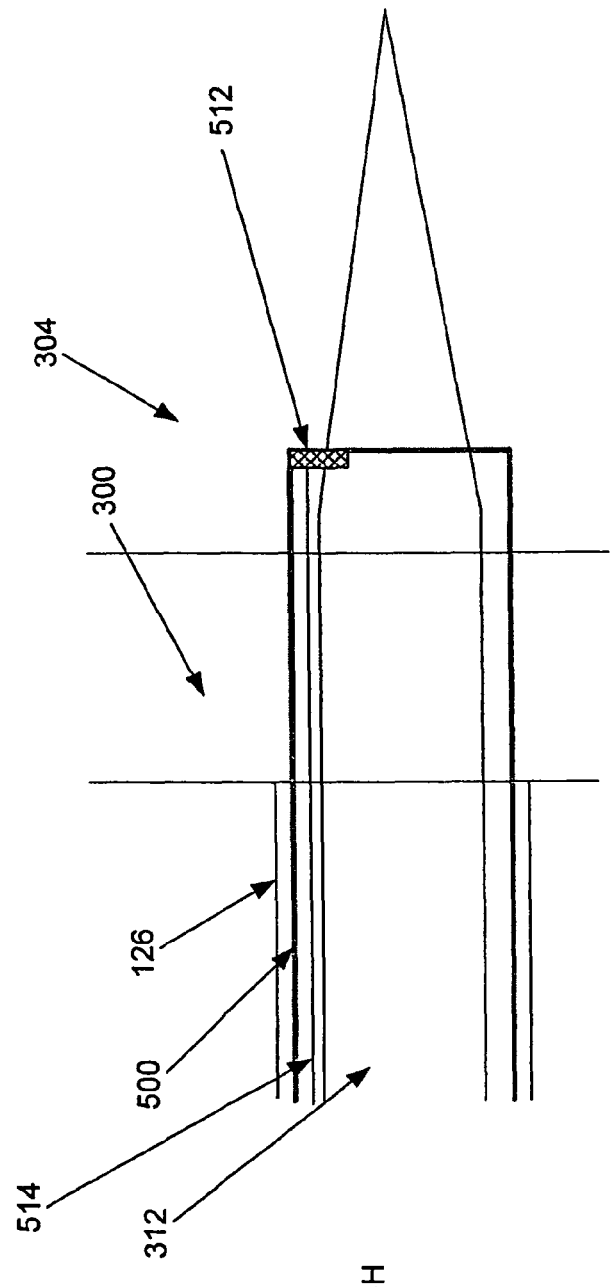
Figure 5G
Figure 5H

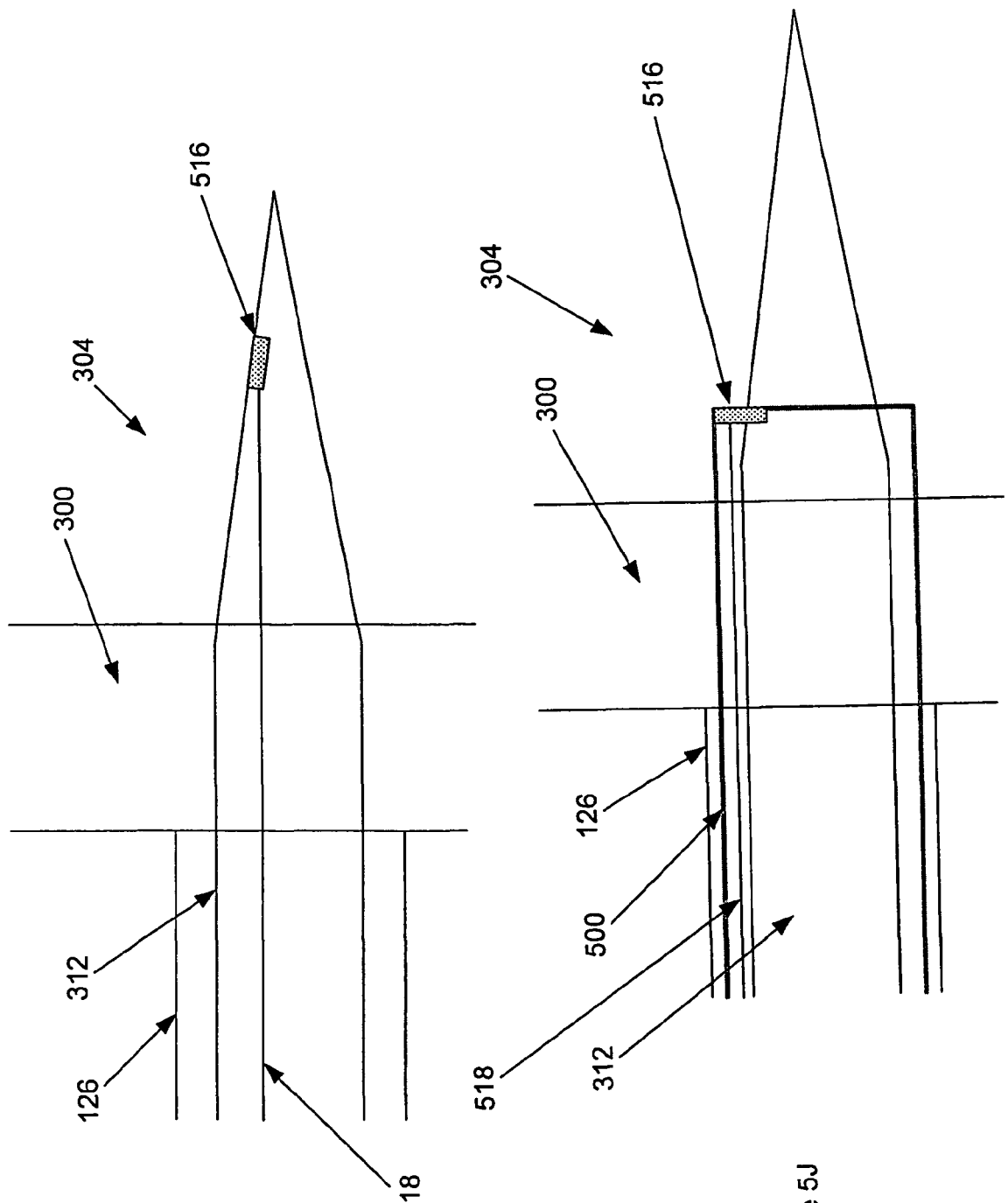

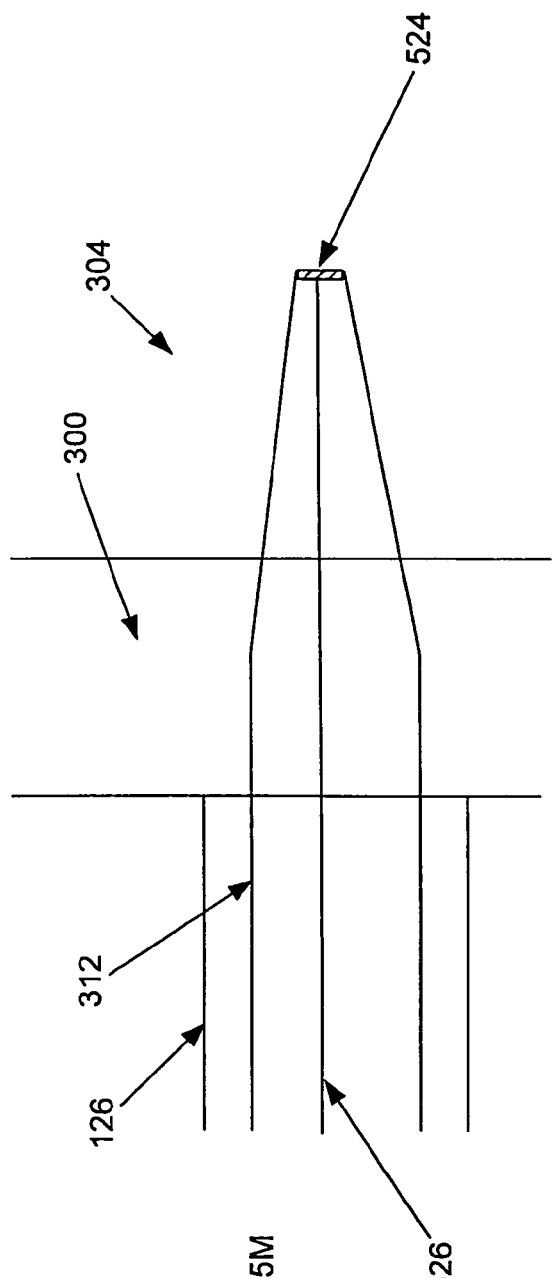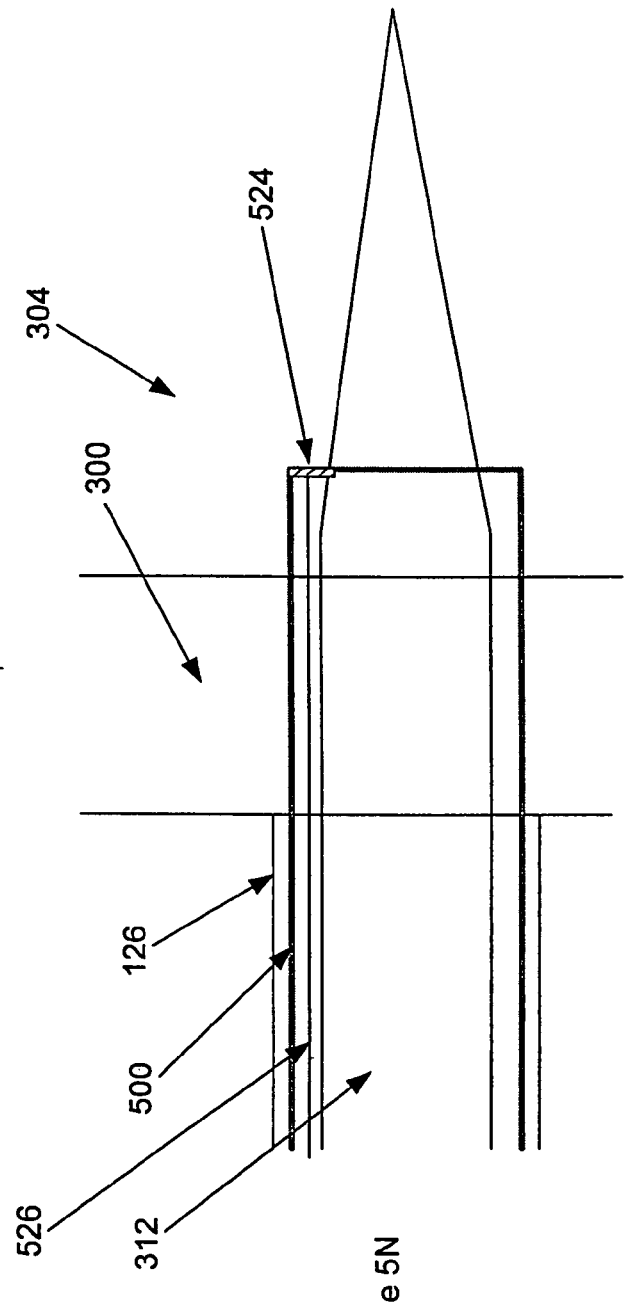

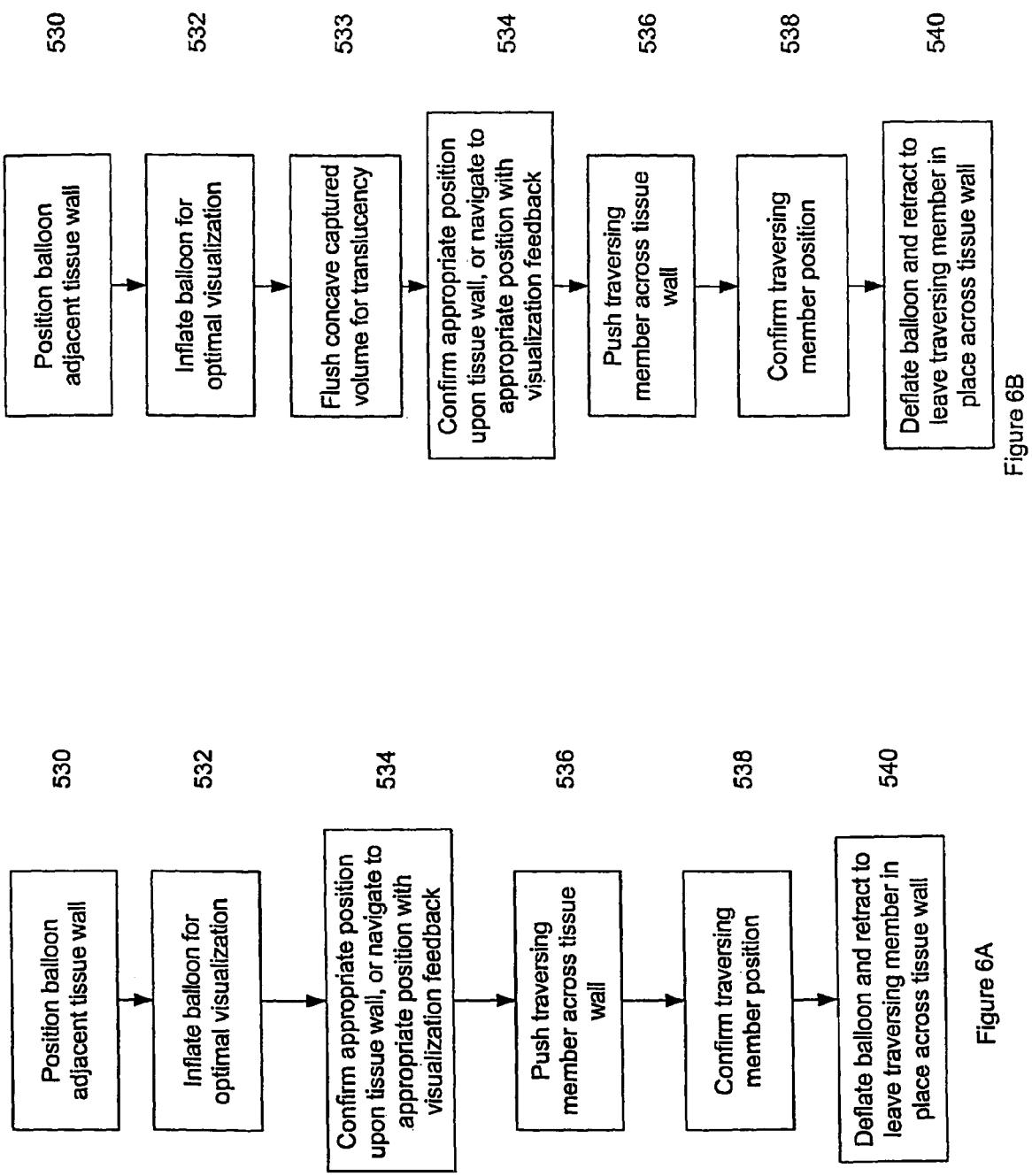

BALLOON VISUALIZATION FOR TRAVERSING A TISSUE WALL

RELATED APPLICATION DATA

This application claims priority to Provisional Application Ser. No. 60/506,293, filed Sep. 25, 2003, the contents of which are fully incorporated herein by reference.

BACKGROUND

One of the challenges in sending a medical device or portion thereof across a an internal body tissue wall is ensuring that the device is not advanced too far past the tissue wall, which can damage adjacent tissue structures. The use of minimally invasive surgical techniques, such as those employing catheters or other elongate surgical probes, complicate this challenge by taking certain aspects of a given medical procedure beyond the normal field of view of the surgeon. For example, conventional minimally invasive techniques for placing a trocar or needle across the atrial septum of a heart involves pushing a transseptal needle, such as those sold by Medtronic/AVE under the tradename "Brockenbrough™", out of a introducer sheath and across the atrial septum, with guidance provided by a conventional imaging modality, such as fluoroscopy.

While conventional techniques, such as "over-the-guidewire" techniques, enable approximate positioning of a transseptal needle adjacent a targeted location upon the atrial septum, there is still no assurance that the needle is correctly positioned before advancement through the tissue wall. Further, it is difficult ascertaining whether the tip of the transseptal device been advanced across the tissue wall and into an adjacent cavity, and whether the cavity is, in fact, the targeted cavity.

BRIEF DESCRIPTION OF THE DRAWINGS

The invention is illustrated by way of example and is not limited to the embodiments in the figures of the accompanying drawings, in which like references indicate similar elements. Further, features shown in the drawings are not intended to be drawn to scale, nor are they intended to be shown in precise positional relationship.

FIG. 1A depicts a side view of a catheter structure in accordance with one embodiment of the invention.

FIG. 1B depicts a cross-sectional view of the structure of FIG. 1A.

FIG. 1C depicts a cross-sectional view of a catheter structure in accordance with another embodiment of the invention.

FIG. 1D depicts a side view of a catheter structure in accordance with yet another embodiment of the invention.

FIGS. 6A and 6B are flow charts illustrating two exemplary procedures for traversing a tissue wall in accordance with embodiments of the invention.

DETAILED DESCRIPTION

Figure 1E:
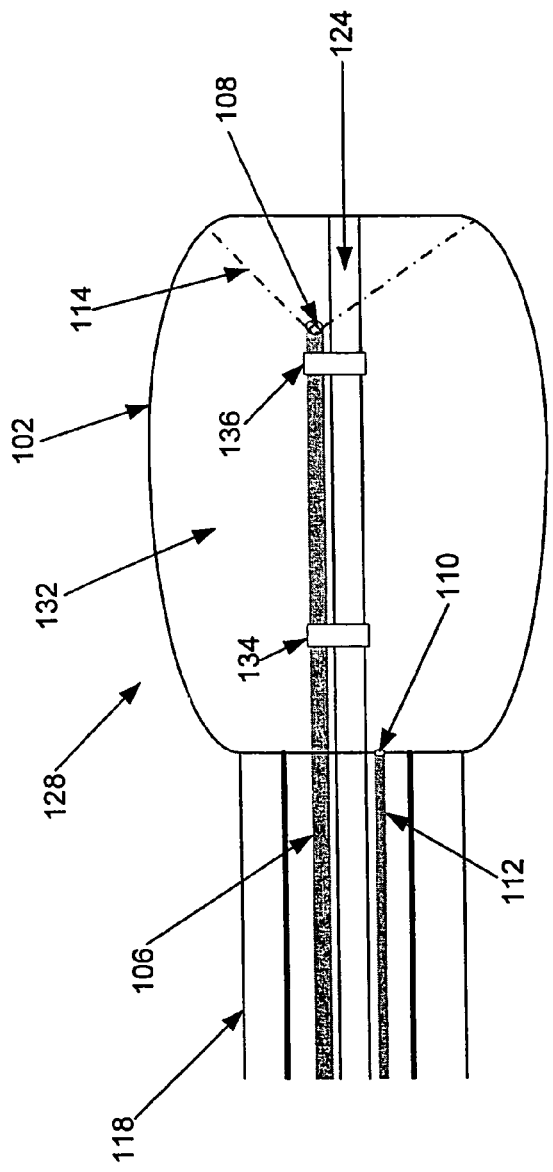
FIG. 1E depicts a side view of a catheter structure in accordance with still another embodiment of the invention.

In the following detailed description of embodiments of the invention, reference is made to the accompanying drawings in which like references indicate similar elements. The illustrative embodiments described herein are disclosed in sufficient detail to enable those skilled in the art to practice the invention. The following detailed description is therefore not to be taken in a limiting sense, and the scope of the invention is to be defined and limited only by the appended claims.

Referring to FIG. 1A, a side view of a distal portion (100) of a catheter in accordance with the present invention is depicted. The same structure is depicted in cross-sectional view in FIG. 1B. In the depicted embodiment, a balloon (102) is disposed at the end of an elongate tubular member (118) which defines various lumens (120, 122, 124) and confines various structures (106, 112) associated with balloon-based optical visualization. A working lumen (124), defined in part by the elongate tubular member (118) and in part by an associated tubular member (126), provides continuous access down the longitudinal axis of the distal portion (100) of the catheter. The tubular member (126) extends from the elongate tubular member (118) to the distal end surface (104) of the balloon, which in the depicted embodiment is substantially flat with the balloon (102) in an inflated or expanded configuration (128). The balloon (102), preferably comprising a translucent polymeric material such as nylon and filled with saline (132) or some other substantially translucent and biologically inert low-viscosity fluid by inflation through one or more balloon sizing lumens (120, 122), provides a medium through which an imaging element (108) may capture images of the tubular member (126) and adjacently positioned objects, such as tissue structures, which fall within the field of view (114) of the imaging element. In another embodiment, the balloon (102) may be inflated with carbon dioxide or another relatively biologically inert gas.

The tubular member (126) also preferably comprises a substantially translucent polymeric material, such as polymethylmethacrylate ("PMMA") or polyimide, paired appropriately with the imaging modality, to enable visualization into and across the tubular member (126) with the imaging element (108). The tubular member may comprise a separate tube component coupled to the distal end of the elongate tubular member (118) utilizing conventional techniques such as polymeric adhesive or stainless steel clips, or may comprise an extension of the material comprising the elongate tubular member (118).

The imaging element (108) may comprise a distal end of an optical fiber, in which case the depicted image transmission line (106) comprises an optical fiber, or it may comprise another image capturing element, such as a charge-coupled-device (CCD) or infrared imaging chip, in which case the image transmission line (106) may comprise an electronic data transmission wire. A lighting element (110) is paired with the imaging element to provide illumination or radiation appropriate for capturing images in the given tissue cavity. In the case of an optical fiber distal end as an imaging element (108), the lighting element (110) preferably comprises an emitter of light, such as a small light bulb, light emitting diode, or end of another optical fiber distal end in communication with an emitter or light. The light energy transmission line (112) may comprise optical fiber, electronic lead wire, or the like to transmit the appropriate lighting energy to the lighting element (110). In another embodiment, the lighting element (110) comprises an emitter of infrared-spectrum radiation and the imaging element (108) comprises an infrared-detecting imaging element to enable infrared-spectrum visualization within the geometrically prescribed field of view (114). Suitable infrared emitters and detectors are well known in the art and available from suppliers such as CardioOptics of Boulder, Colo.

The imaging element (108) may comprise a lens, filter, mirror, or other structure configured to control the field of view (114) or focal length of the associated imaging element (108). Further, a lens, filter, mirror, or other structure may be positioned distally from the imaging element (108) within the balloon portion (116) of the catheter distal end (100) for similar purposes. The utilization of a imaging element (108) located at the distal end of a medical instrument, such as a balloon catheter, for purposes of visualizing objects from the point of interest is referred to herein as "direct visualization". In other words, "direct visualization" is used in reference to placing an imaging "eye" distally to the location of tissue treatment interest.

Referring to FIG. 1B, a cross-sectional view of the structures of FIG. 1A depicts the balloon sizing lumens (120, 122), working lumen (124), imaging element (108), and lighting element (110) in a substantially aligned configuration which is more resistive to cantilever bending of the catheter distal end (100) along the direction of the aligned configuration than in a direction 90-degrees rotated from such alignment. In another embodiment, as shown in FIG. 1C, such componentry is cross-sectionally arranged as tightly as possible about the central axis of the elongate tubular member (118) to facilitate easier and more uniform cantilever bending. Such components may be arranged within the elongate tubular member (118) to facilitate overall mechanical performance goals given the mechanics of the components themselves. For example, in an embodiment where high cantilever-bending flexibility in all directions is desired, and wherein the image transmission line (106) and light energy transmission line (112) comprise relatively stiff optical fiber, it is advantageous to position these two structures (106, 112) close to the central axis of the elongate tubular member (118).

The elongate tubular member (118) preferably comprises a conventional polymeric material, such as that sold under the trade name "Pebax™" by Atofina Corporation, which is suitable for use inside of animals and has desirable mechanical and manufacturing properties. In the case of optical fiber, glass fibers, such as those conventionally utilized in endoscopes, may be utilized, or more flexible polymeric optical fibers, such as those available from Nanoptics Corporation of Gainesville, Fla., may be utilized.

FIG. 1D depicts a structure similar to that of FIG. 1A, with the exception that the balloon (102) is in a deflated or contracted configuration (130), as the result of a removal of saline (132) from the balloon (102) via the balloon sizing lumens (120, 122). In one embodiment, one of the balloon sizing lumens (120) is reserved only for inflation, while the other (122) is reserved for deflation. More or less than two balloon sizing lumens may be suitable, depending upon the diameter of such structures and desired rate of inflation and deflation, as would be apparent to one skilled in the art. As shown in FIG. 1D, the contracted (130) balloon preferably has an outer diameter roughly the same size as the associated elongate tubular member (118) for atraumatic, smooth endolumenal delivery while also facilitating a narrowed forward-looking field of view (115) with the imaging element (108) during delivery.

Referring to FIG. 1E, another embodiment is depicted wherein the imaging element (108) is positioned forward within the balloon (102) to gain better access to adjacent objects of interest adjacent the distal end of the balloon (102) and within the field of view (114) of the imaging element (108) and broadcast range of the lighting element (110). With such a configuration the image transmission line (106) extends beyond the distal end of the elongate tubular member (118) and into the balloon (102), as depicted in FIG. 1E. The portion of the image transmission line (106) within the balloon (102) may be mechanically stabilized with small polymer or metallic clips (134, 136), as shown.

Figure 1F:
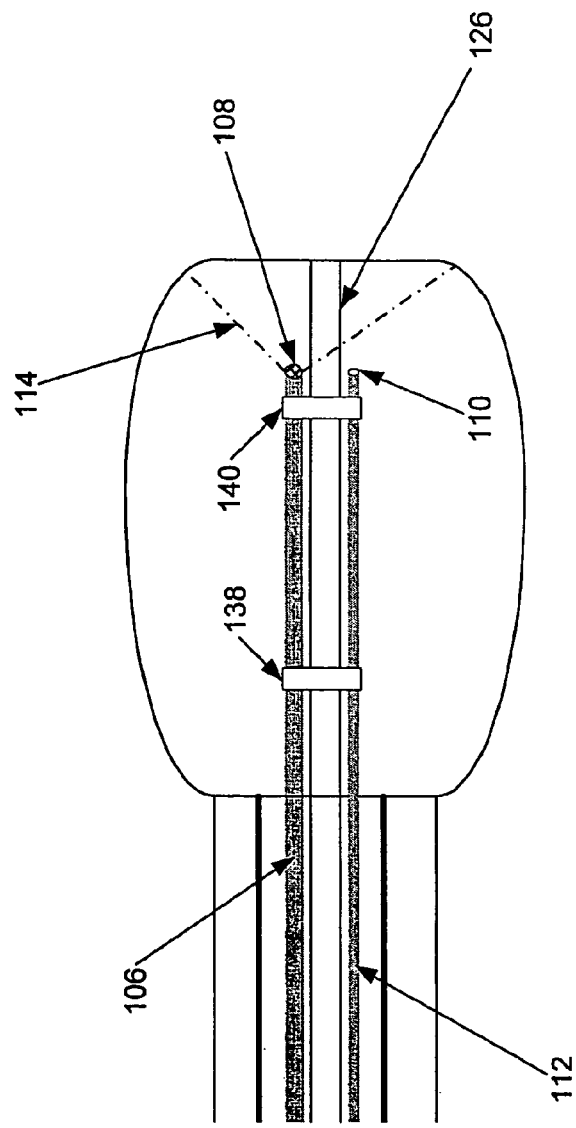
FIG. 1F depicts a side view of a catheter structure in accordance with yet another embodiment of the invention.

Referring to FIG. 1F, another embodiment is depicted wherein the lighting element (110) is positioned forward into the balloon (102) with the imaging element (108) to minimize shadowing effects. Mechanical stabilizers (138, 140) similar to those described in reference to FIG. 1E may be utilized to maintain the relative positioning of the balloon (102), tubular member (126), imaging element (108), and lighting element (110).

Figure 2:
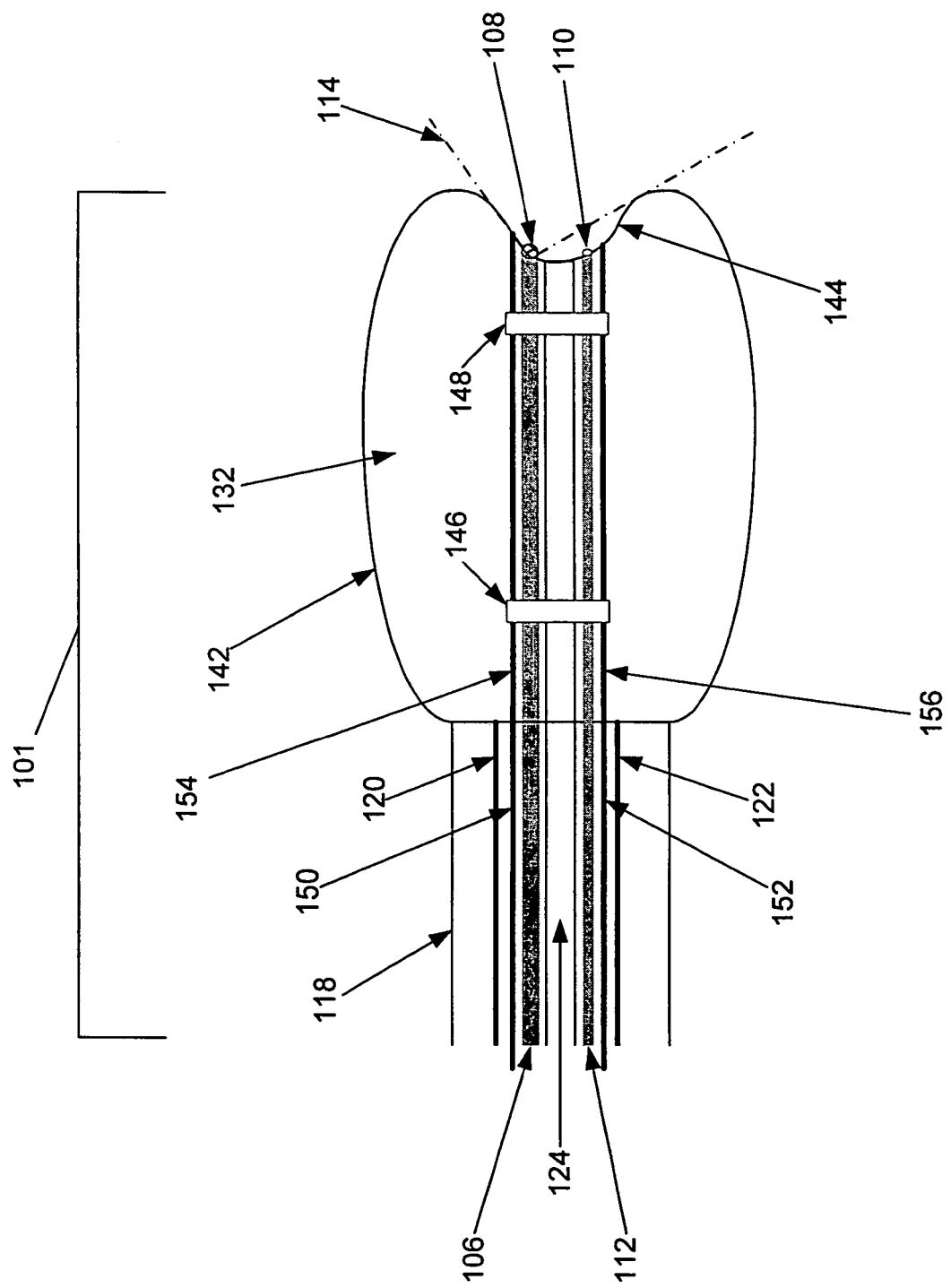
FIG. 2 depicts a side view of a catheter structure in accordance still another embodiment of the invention.

Referring to FIG. 2, another embodiment is depicted wherein the balloon (102) comprises a concave surface (144) distally upon inflation, and wherein the imaging element (108) and lighting element (110) are positioned for substantially immediate visualization of adjacently positioned objects. With such a configuration, it may be necessary or preferable to flush and fill a volume defined by the concave surface (114) and an immediately interfaced object with a translucent, high-viscosity, and biologically inert fluid such as saline, or biologically inert gas, utilizing additional fluid delivery lumens such as those depicted (150, 152) in FIG. 2. Such lumens (150, 152) are extended through the balloon (102) to the concave surface (144) by small tubular members (154, 156), which may be stabilized along with the other associated structures within the balloon (102) utilizing mechanical stabilizers (146, 148) similar to those described in reference to FIG. 1E, as shown in FIG. 2.

Figure 3A:
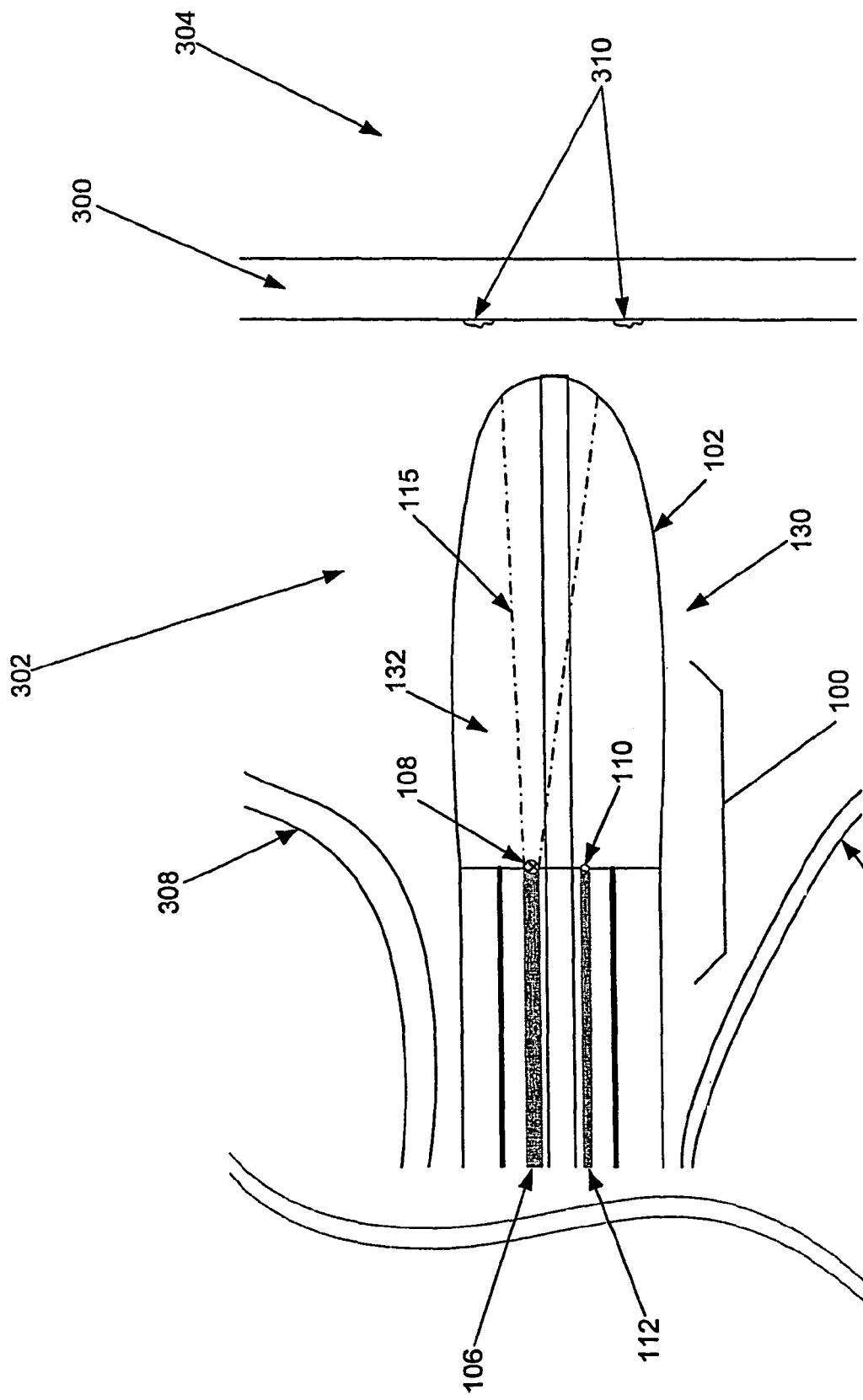
FIGS. 3A-3F are side views depicting various stages of yet another catheter structure embodiment of the invention, including a traversing member traversing a tissue wall in a body.

Referring to FIGS. 3A-3F, one embodiment of a method for using structures such as those described in reference to FIGS. 1A-1F is depicted. Utilizing conventional techniques, the distal end of the catheter (100) is positioned in the vicinity of a targeted tissue structure or tissue wall (300). As shown in FIG. 3A, the distal end (100) may be advanced through a relatively tight geometry between two tissue structures (306, 308) and into a first enlarged cavity (302), which may be opposite the targeted tissue wall (300) from a second enlarged cavity (304). A targeted region of the tissue wall (300) may be identifiable by terrain or substructures (310) comprising the surface of the targeted tissue wall (300).

As the contracted (130) balloon (102) approaches the substructures (310), a narrowed field of view (115) captured by the imaging element (108) as facilitated by the lighting element (110) may be utilized for navigating the balloon (102) into position adjacent the tissue wall (300). In a substantially nontranslucent media such as blood within the first cavity (302), visualization of the substructures or tissue wall may not be useful until the distal end of the balloon is very close to the tissue wall (300), whereas in a more translucent media, such as saline or carbon dioxide, targeted tissues and substructures may become visible as soon as they are within a direct field of view, depending upon the focal characteristics of the imaging element (108), as would be apparent to one skilled in the art. Further, the translucent media within the balloon (102) may comprise a contrast agent to facilitate imaging. For example, in the case of a conventional fluoroscopic imaging modality, the translucent media preferably comprises a conventional contrast agent such as iodine.

Figure 3B:
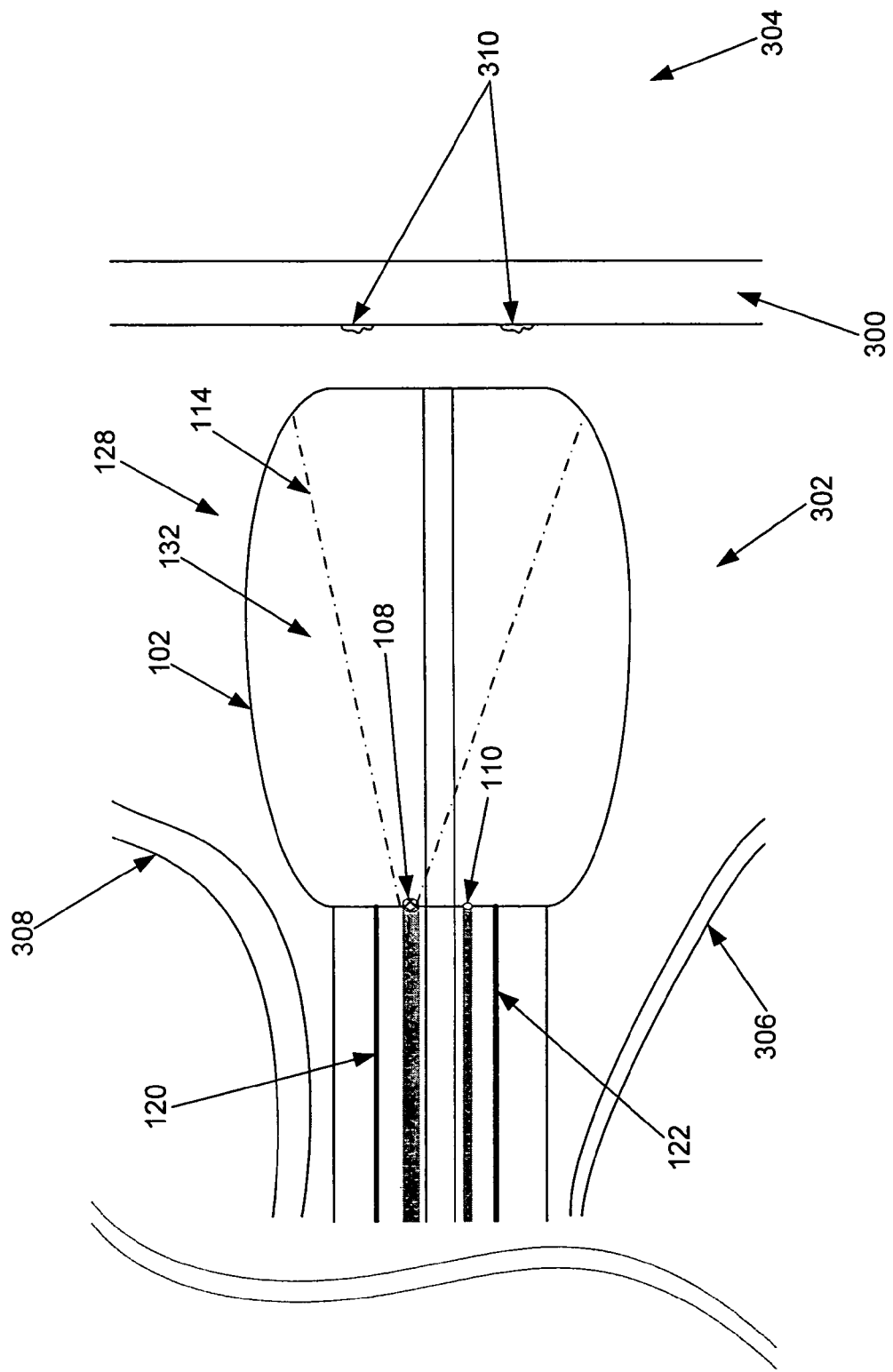

Upon entry into a relatively large cavity (302), the balloon may be inflated to provide a broadened field of view and illumination, as shown in FIG. 3B. Positioning of the balloon (102) relative to the first enlarged cavity (302) may be confirmed or monitored using conventional techniques, such as ultrasound and fluoroscopy.

Figure 3C:
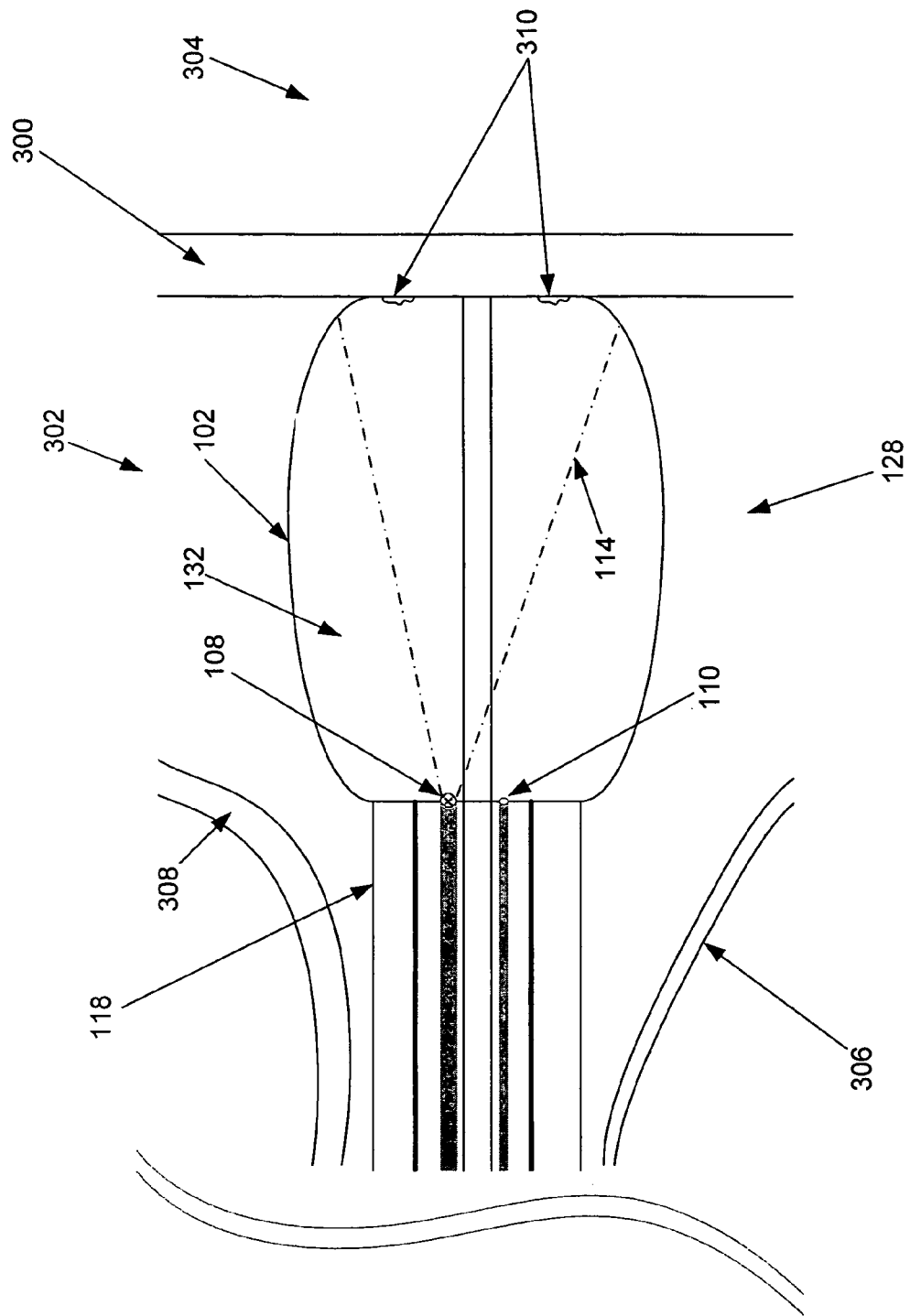

Referring to FIG. 3C, the expanded balloon is advanced into contact with the targeted tissue wall (300), where even with a nontranslucent cavity (302) media such as blood, the tissue wall (300) and substructures thereof (310) may be visualized through the balloon (102) with the imaging element (108) and lighting element (110). With such visualization, it may be preferable to fine-tune the position of the balloon relative to the tissue wall (300).

Figure 3D:
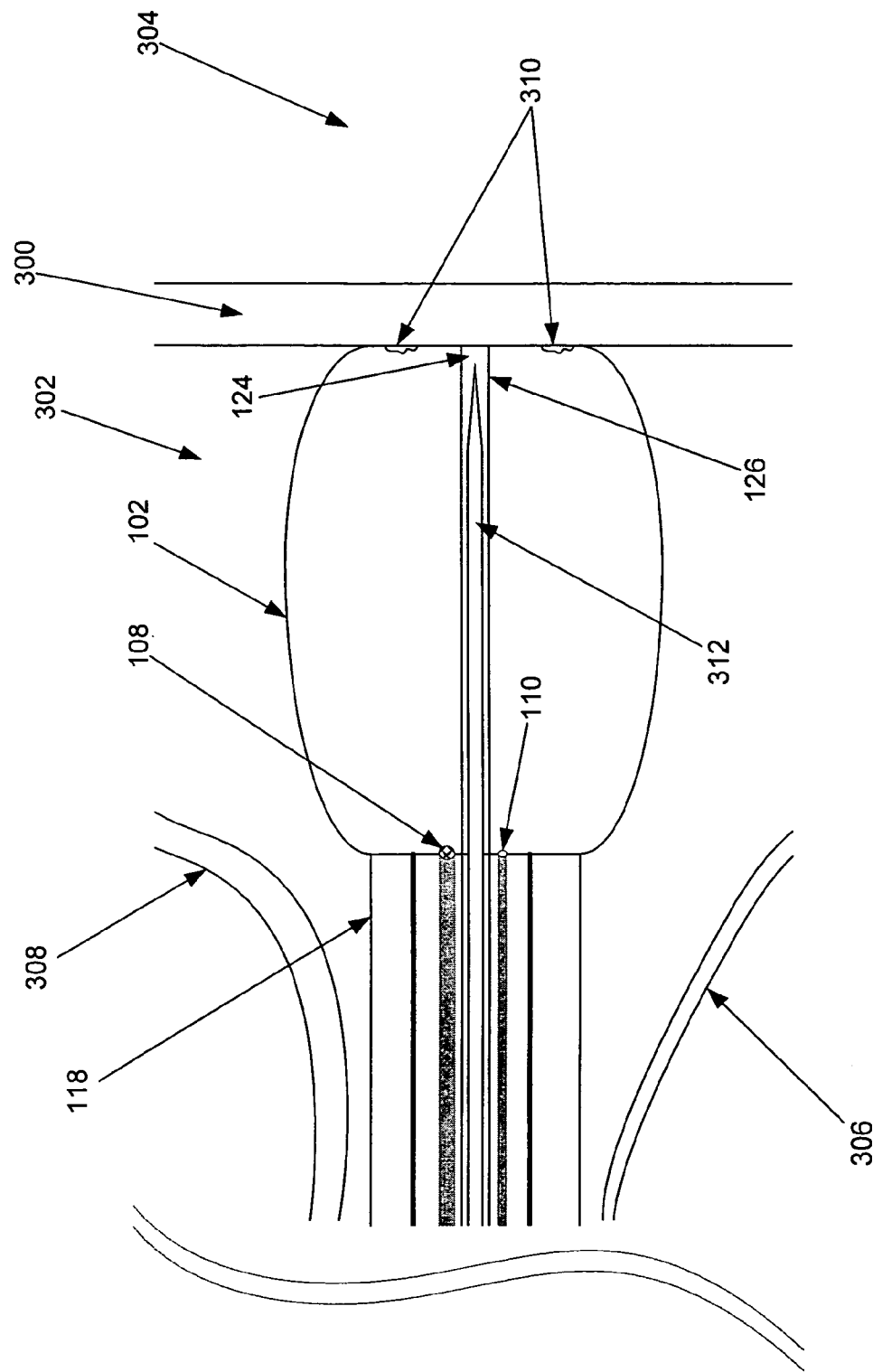
Figure 3E:
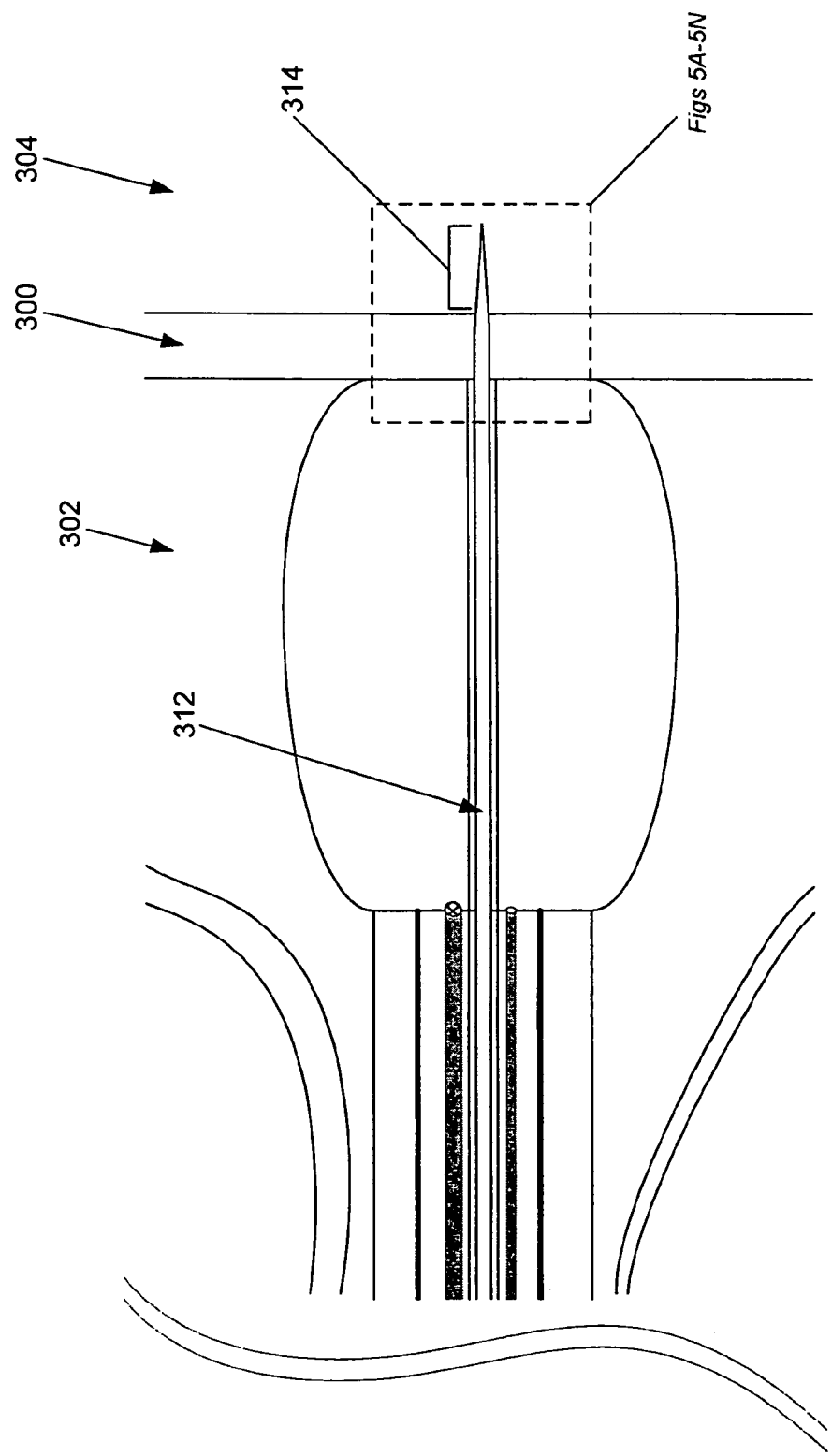

Referring to FIG. 3D, a tissue traversing member, such as a trocar or Brockenbrough™ needle, is advanced through the working lumen (124) of the elongate tubular member (118) and tubular member (126) to a position adjacent the targeted tissue wall (300). As described in reference to FIGS. 1A and 1B, the tubular member (126) preferably comprises a material through which the imaging element (108) can "see" to provide the user with feedback regarding the relative positioning of the traversing member (312), balloon (102), and tissue wall (300). After confirmation of preferred alignment of these structures, the traversing member (312) is advanced into and across the tissue wall (300), as depicted in FIG. 3E. Visualization of gradient markers (not shown) on the traversing member (312), along with images of the pertinent structures from other modalities, such as fluoroscopy and/or ultrasound, facilitate precise positioning of a portion of the traversing member (312) across and beyond (314) the subject tissue wall (300), into the second cavity (304). Further details of the traversal positioning and confirmation are described in reference to FIGS. 5A-5N. While the illustrative description in reference FIGS. 3A-3E incorporates a balloon catheter structure similar to that of FIG. 1A, such description is applicable to embodiments such as those depicted in FIGS. 1E and 1F and FIG. 2, with the exception that the structures similar to FIG. 2 may involve additional steps, as further described in reference to FIG. 4 and FIG. 6B.

Figure 3F:
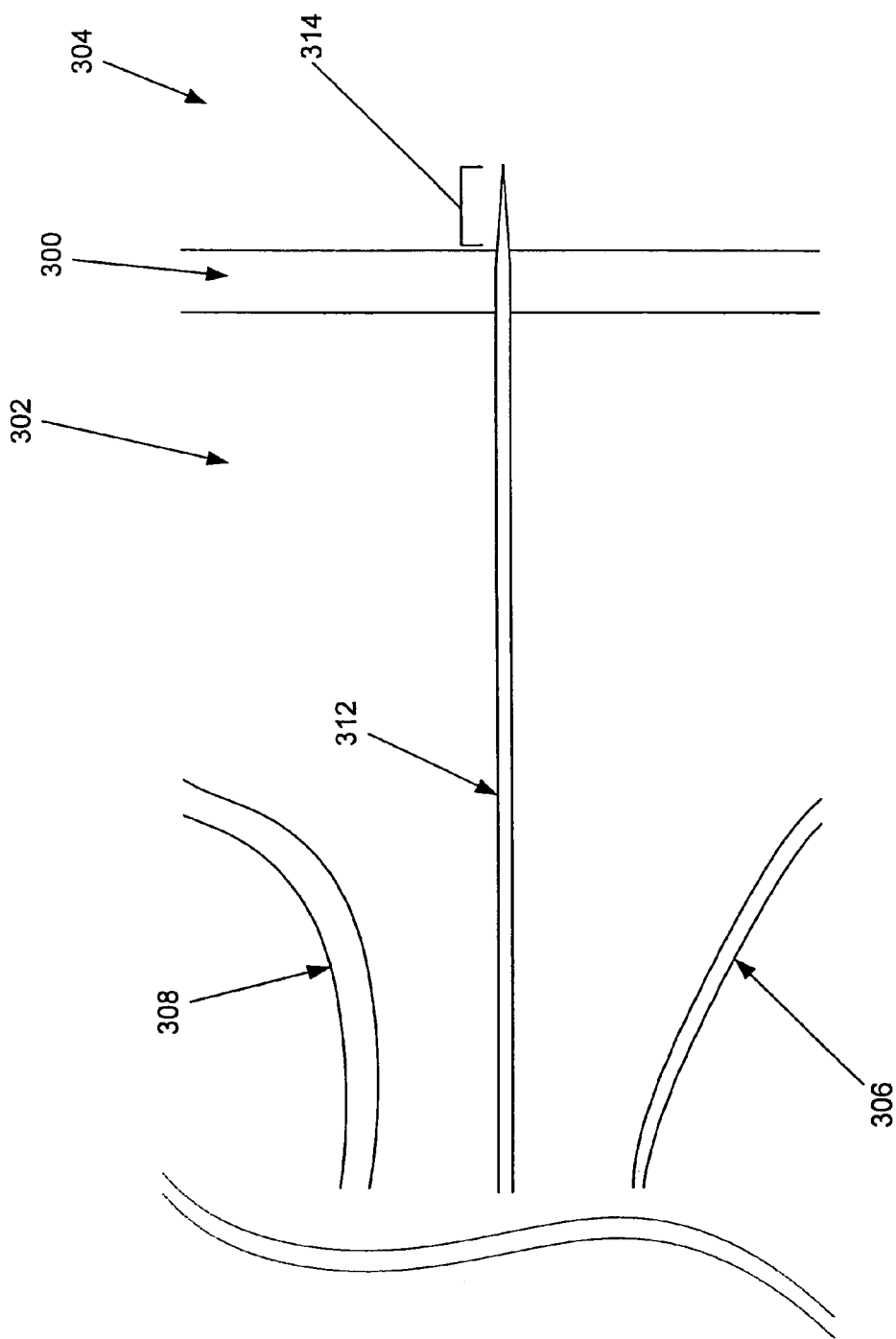
Figure 3G:
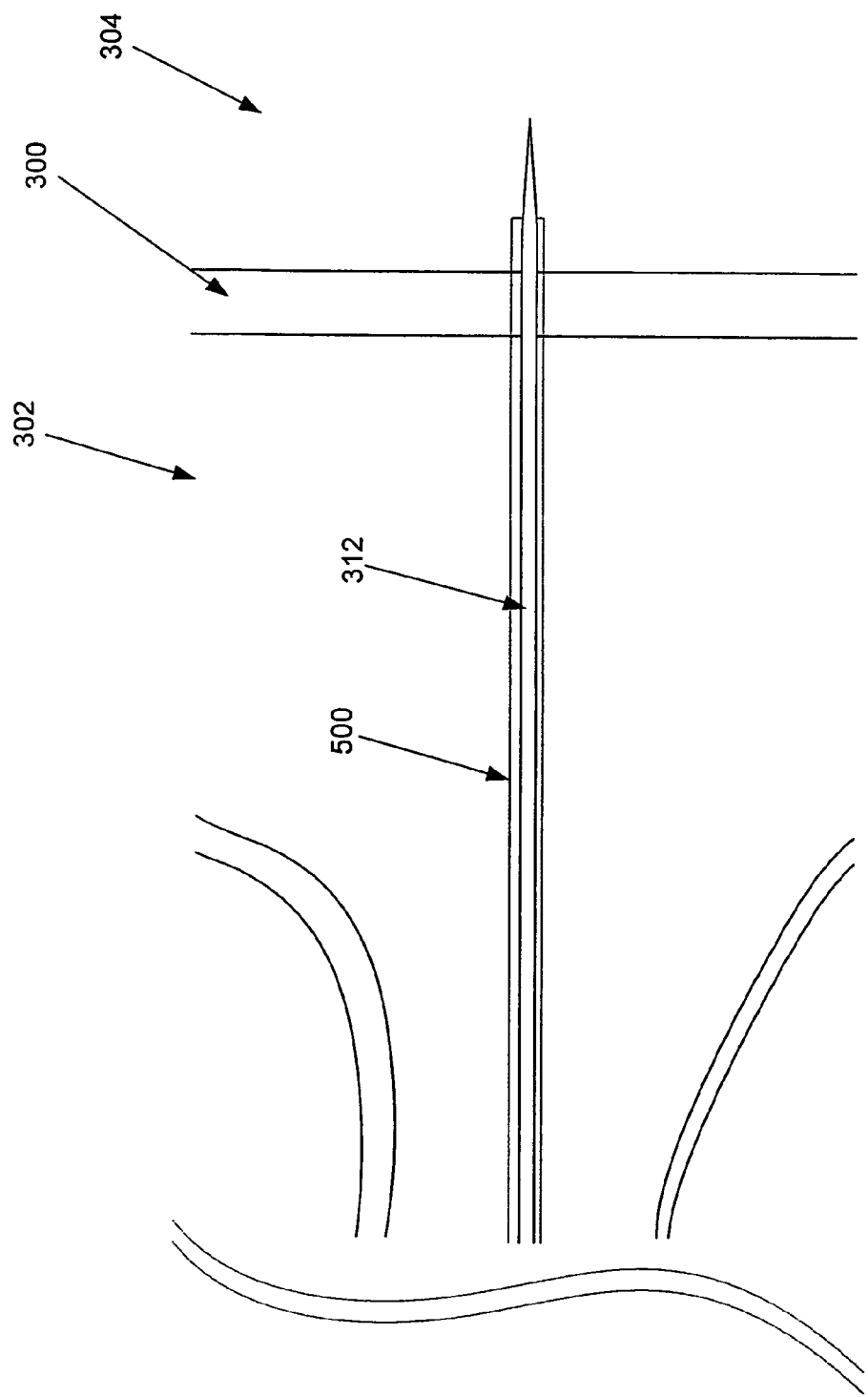
FIGS. 3G-3I are side views of a variation of the embodiment of FIGS. 3A-F, in which sleeve is left positioned after withdrawal of the tissue traversing member to function as an access lumen across the tissue wall.
Figure 3H:
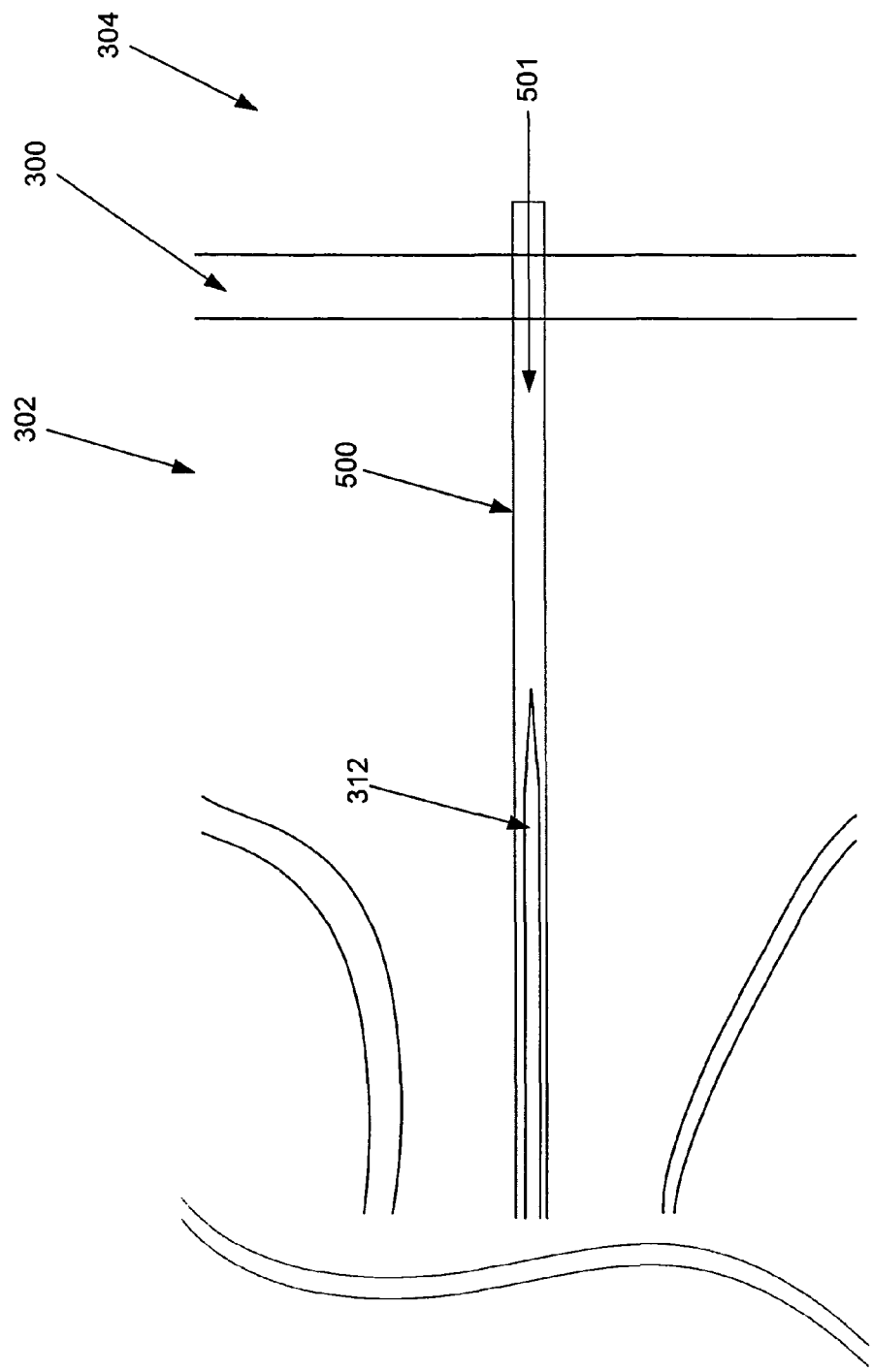
Figure 3I:
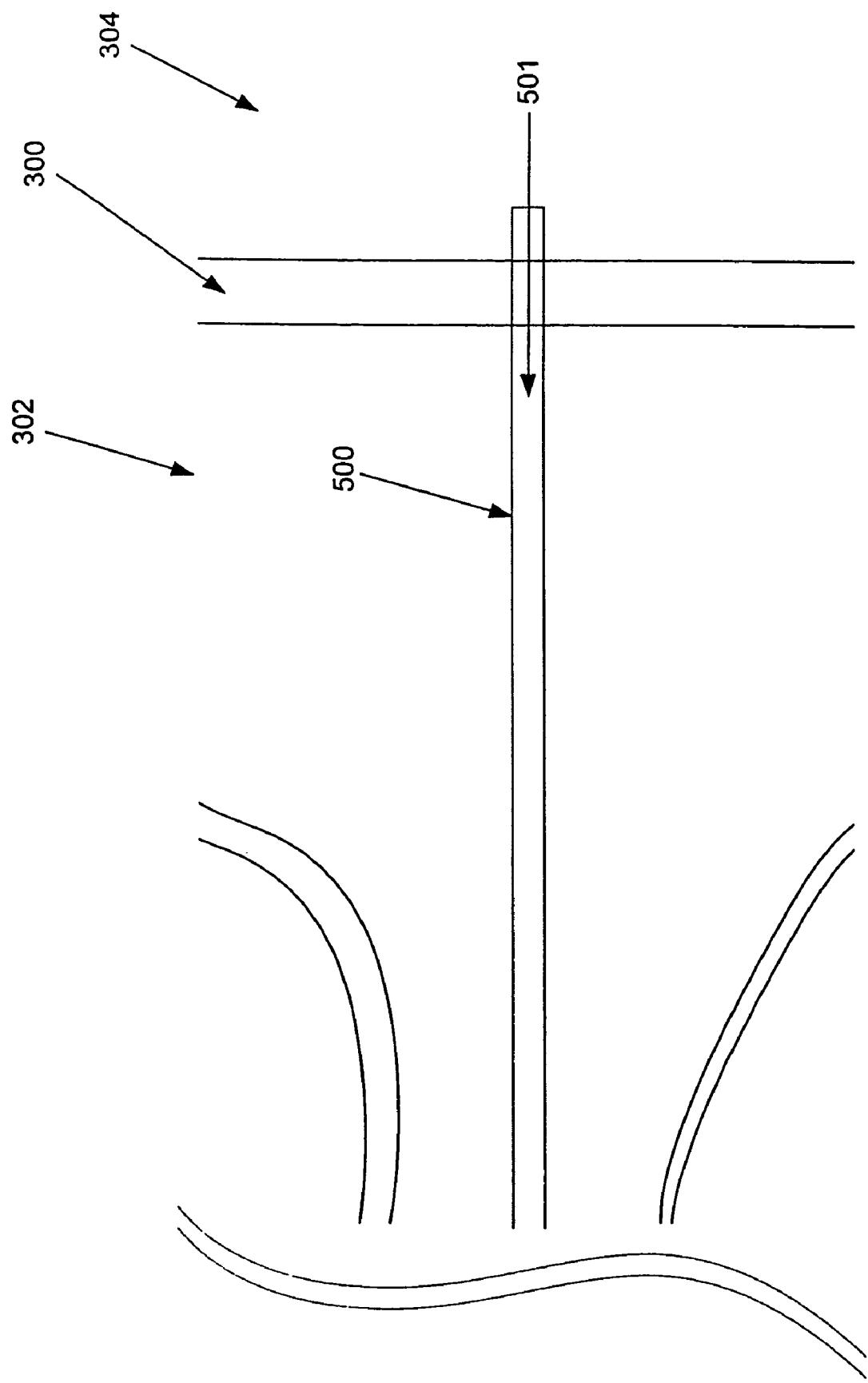

Referring to FIG. 3F, subsequent to traversal and confirmation of desired positioning of the traversing member (312), the distal end of the catheter may be withdrawn, leaving behind the (312). As depicted in FIG. 3G, in another embodiment, the traversing member (312) is advanced into place accompanied with a preferably tubular sleeve (500) which may be left in place along with the traversing member (312) following withdrawal of the catheter. Referring to FIGS. 3H and 3I, the traversing member (312) may subsequently be withdrawn, leaving behind only the sleeve (500), which provides an access lumen (501) over to the second cavity (304), the access lumen being usable as a working lumen for tools, injections, and the like which may be used to examine and treat the second cavity (304), tissue wall (300), or other adjacent tissues.

Figure 4:
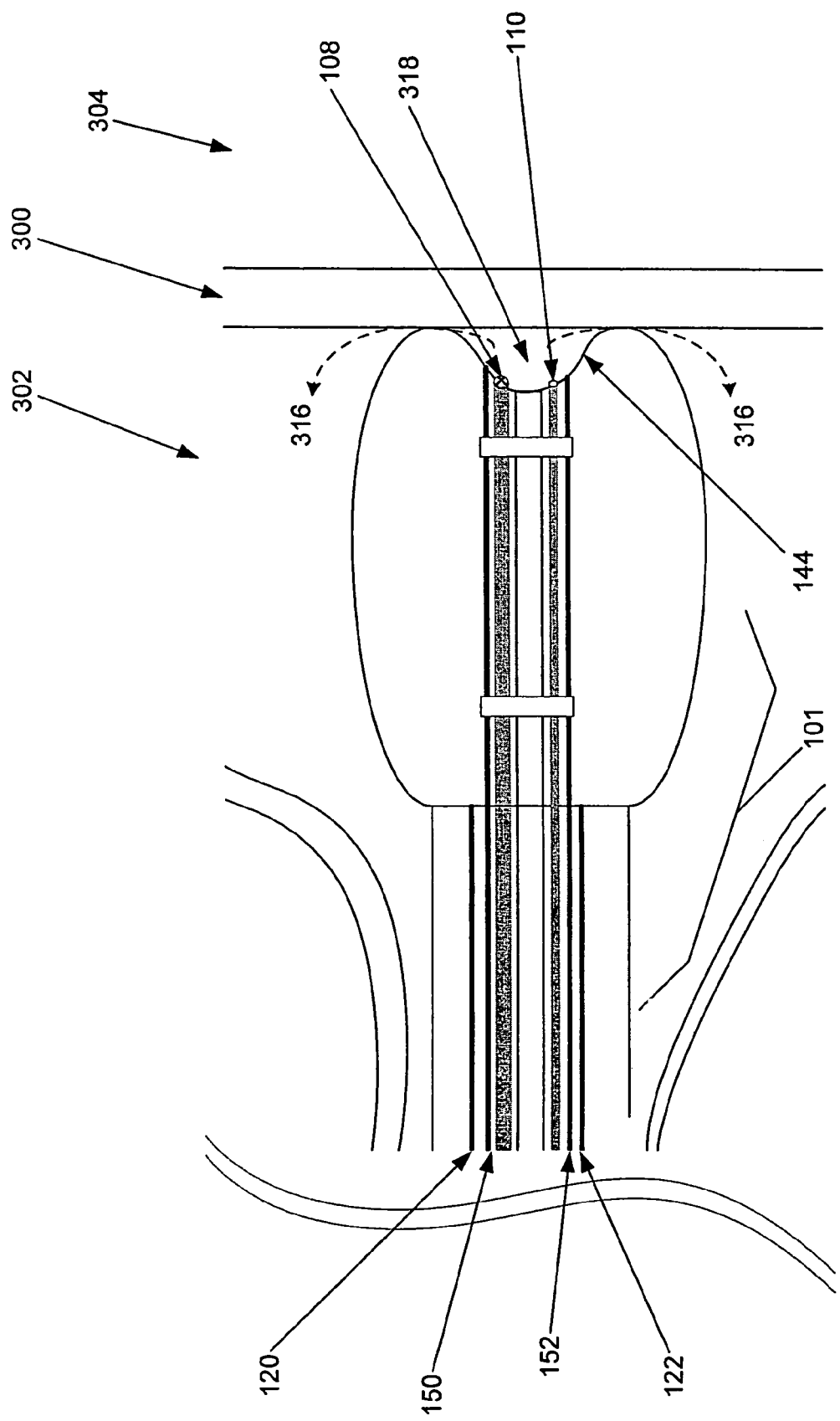
FIG. 4 is a side view depicting use of a catheter structure embodiment similar to that depicted in FIG. 2.

Referring to FIG. 4, a depiction of a catheter distal end (101) similar to that depicted in FIG. 2 is illustrated in a position analogous to the positioning of structures of FIG. 3C to illustrate the notion that a flushing of substantially translucent fluid (316) may be utilized to facilitate viewing by the imaging element (108) and lighting element (110) through a volume (318) captured between the concave surface (144) of the depicted embodiment and a tissue wall (300).

Figure 5A:
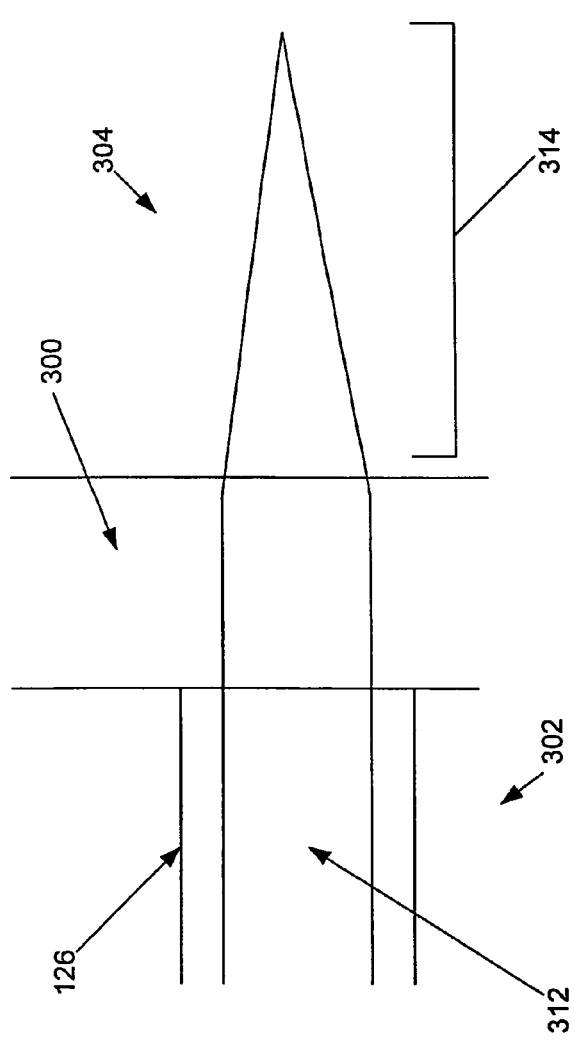
FIGS. 5A-5N depict various structures for confirming a position of a traversing member relative to a tissue wall in accordance with various embodiments of the invention.
Figure 5B:
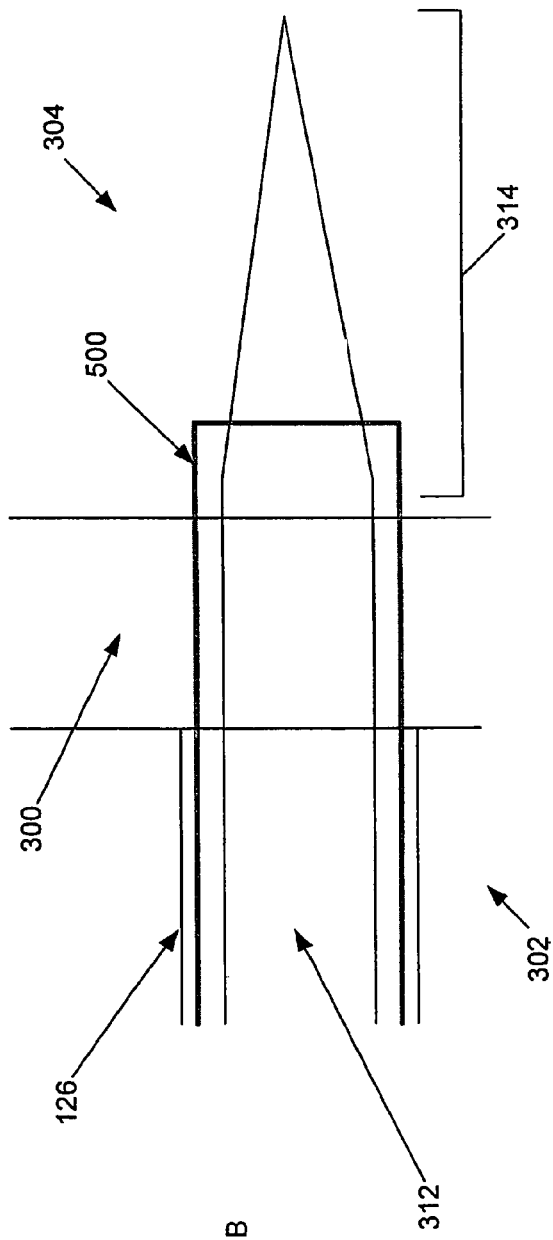

Referring to FIG. 5A, a close-up side view depicting an embodiment of a traversing member (312) positioned across a tissue wall (300) is depicted. As shown in FIG. 5A, the traversing member (312) is guided to the tissue wall (300) by the tubular member (126). The distal tip (314) of the traversing member is positioned in the cavity (304) opposite the cavity (302) in which the tubular member (126) is positioned. Referring to FIG. 5B, a close-up side view depicting an embodiment of a traversing member (312) with a sleeve (500) is illustrated, with the sleeve (500) and traversing member (312) both advanced into a position across the tissue wall with distal protrusion (314) into the cavity (304) opposite the cavity in which the tubular member (126) is positioned.

FIGS. 5C-5D, 5E-5F, 5G-5H, 5I-5J, 5K-5L, and 5M-5N depict pairings of embodiments analogous to the sleeveless and sleeved embodiments depicted in FIGS. 5A and 5B. Each of these pairings features a different embodiment for confirming the position of a traversing member (312) across a subject tissue wall (300) by sensing or monitoring a difference known to be associated with a desired second cavity (304) position or position within the targeted tissue wall (300). For example, localized pressure within a first cavity (302) may be substantially different than both the localized pressure within the tissue wall (300) and within a second cavity (304).

Likewise, for flow rate, oxygen saturation, etcetera, as described in reference to FIGS. 5C-5N. Each of the different monitoring variables is described separately in FIGS. 5C-5N, but, as would be apparent to one skilled in the art, the monitoring structures and modalities may be combined for increased position determination capability. For example, in one embodiment it is desirable to sense both pressure changes and echo timing for redundancy in determining whether the distal tip (314) of a traversing member (312) and/or sleeve (500) is within a first cavity (302), tissue wall (300), second cavity (304), or perhaps an undesirable location in a third cavity, such as a major blood vessel with a substantially high flow rate as detected by Doppler and distinguished from a targeted destination cavity.

Figure 5C:
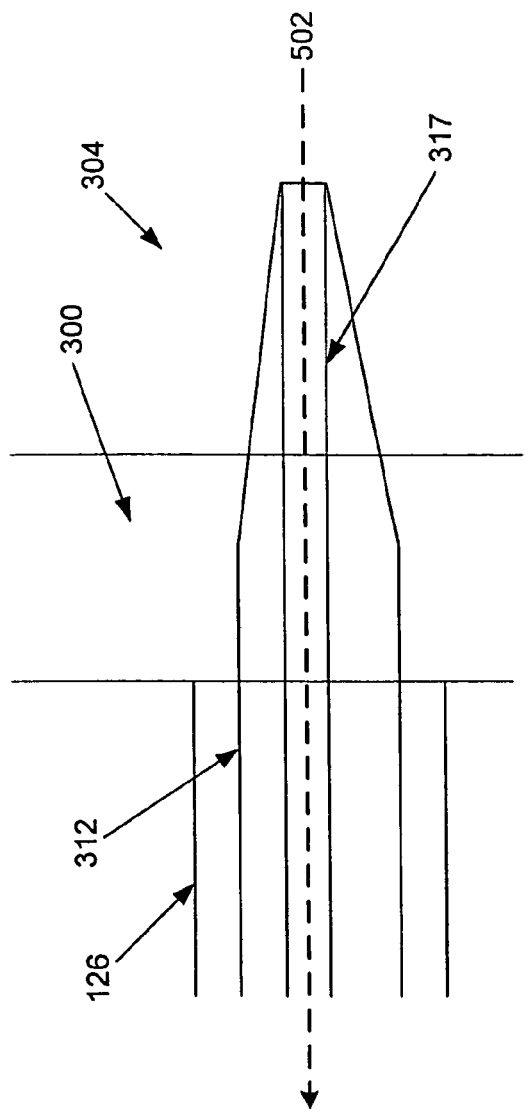
Figure 5D:
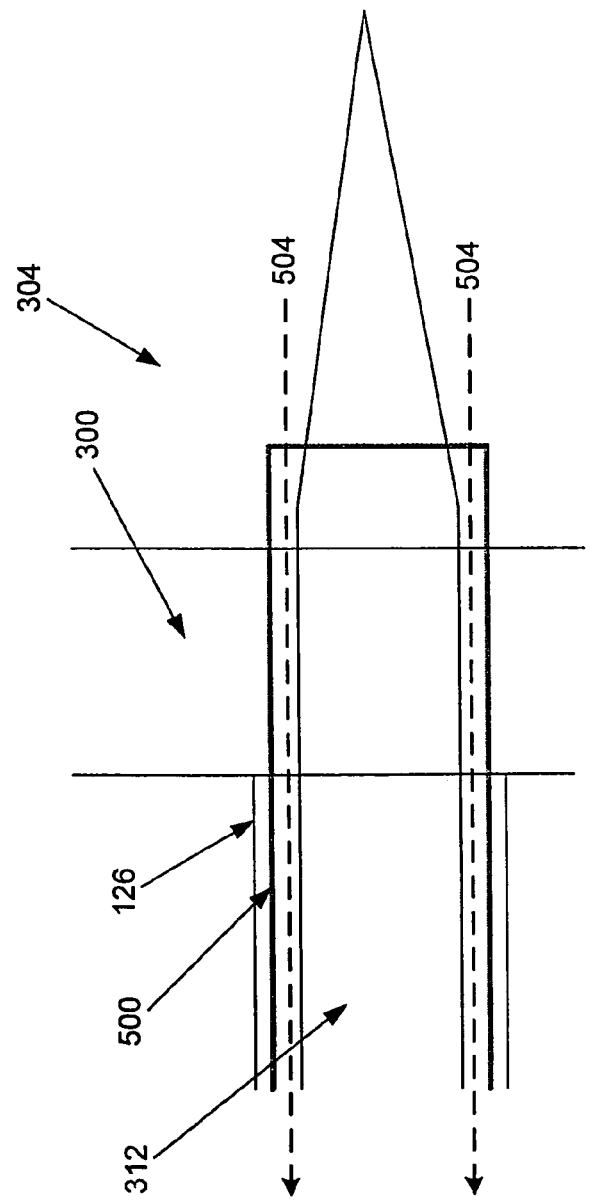

Referring to FIG. 5C, the location of the traversing member (312) may be determined by sampling fluid along a pathway (502) through a lumen (317) formed in the traversing member (312), and transporting sampled fluid proximally to a position outside of the body for conventional testing, such as rapid chemical testing, pulse oximetry, and the like. A traversing member (312) defining such a lumen (317) could be formed using conventional technologies, and purchased from suppliers of high-precision machined trocars and similar structures such as Disposable Instrument Company, Inc. of Shawnee Mission, Kans. FIG. 5D depicts a sleeved embodiment wherein fluid is sampled along a pathway (504) between the traversing member (312) and the sleeve (500). Referring back to FIG. 3I, the lumen (501) of an empty sleeve (500) may serve a similar purpose.

Figure 5E:
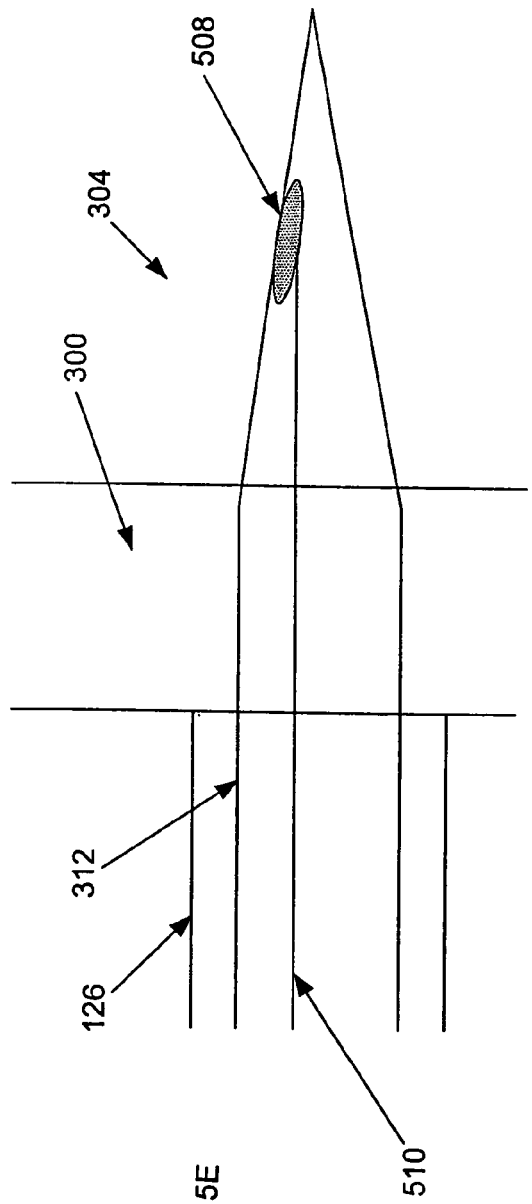
Figure 5F:
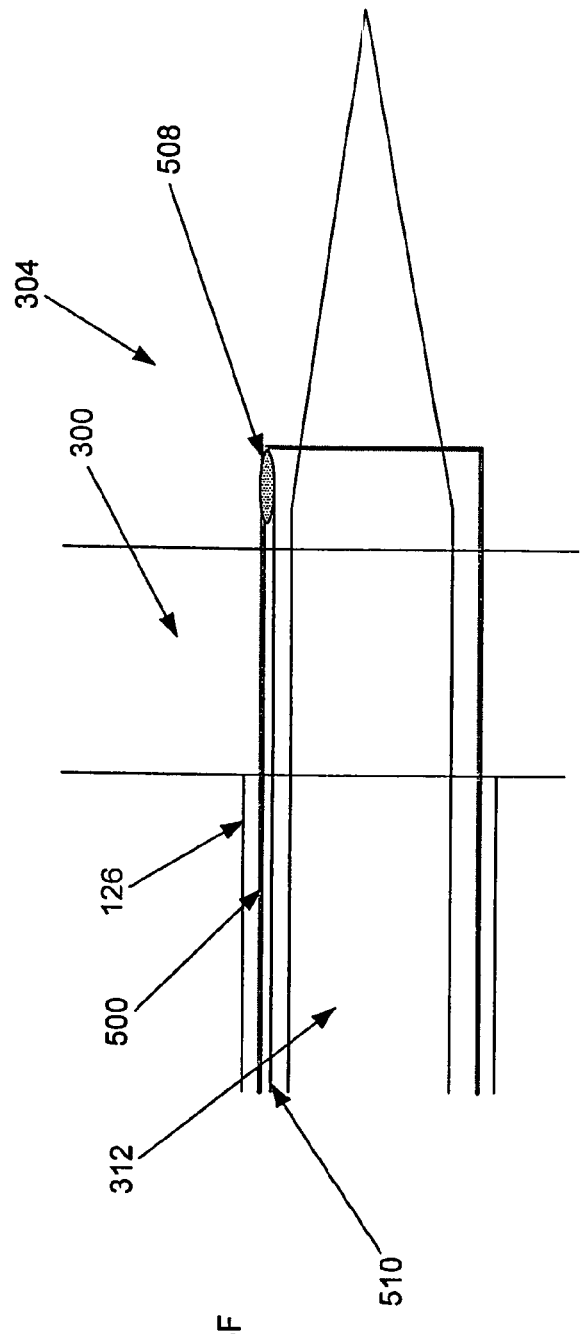

Referring to FIG. 5E, a traversing member (312) having a distally disposed pressure sensor (508) with a sensor lead (510) may be utilized to monitor pressure changes at the distal portion of the traversing member (312). Suitable small pressure sensors (508) are known in the art and available from suppliers such as Motorola Sensor Products of Phoenix, Ariz., and IC Sensors, a division of Measurement Specialties, of Milpitas, Calif. FIG. 5F depicts an embodiment wherein a pressure sensor (508) is coupled to a sleeve (500).

Referring to FIG. 5G, a color shade sensor (512) is coupled to the distal portion of a traversing member (312) to facilitate monitoring of the color or graytone of local objects such as aterial versus venous blood. The color shade sensor (512) preferably comprises a CCD or CMOS-based image sensor, such as those available from suppliers such as Eastman Kodak Image Sensor Solutions, which is configured in this embodiment to transmit data proximally through a sensor lead (514) as depicted. FIG. 5H depicts an embodiment wherein a color shade sensor (512) is coupled to a sleeve as opposed to directly to the traversing member (312). As would be apparent to one skilled in the art, mirrors, lenses, filters, and the like may be utilized to enhance or modify the image sampling of such sensors.

Referring to FIG. 5I, an oxygen saturation sensor (516) is coupled to the distal end of a traversing member (312) to facilitate monitoring of the partial pressure of oxygen at the oxygen saturation sensor (516) location utilizing a sensor lead (518). As shown in FIG. 5J, an oxygen saturation sensor (516) may also be positioned upon a sleeve (500). Small oxygen saturation sensors, generally comprising a small radiation transmitter, such as a laser diode, and a small radiation receiver, are available from suppliers such as Nellcor Puritan Bennett of Pleasanton, Calif.

Figure 5K:
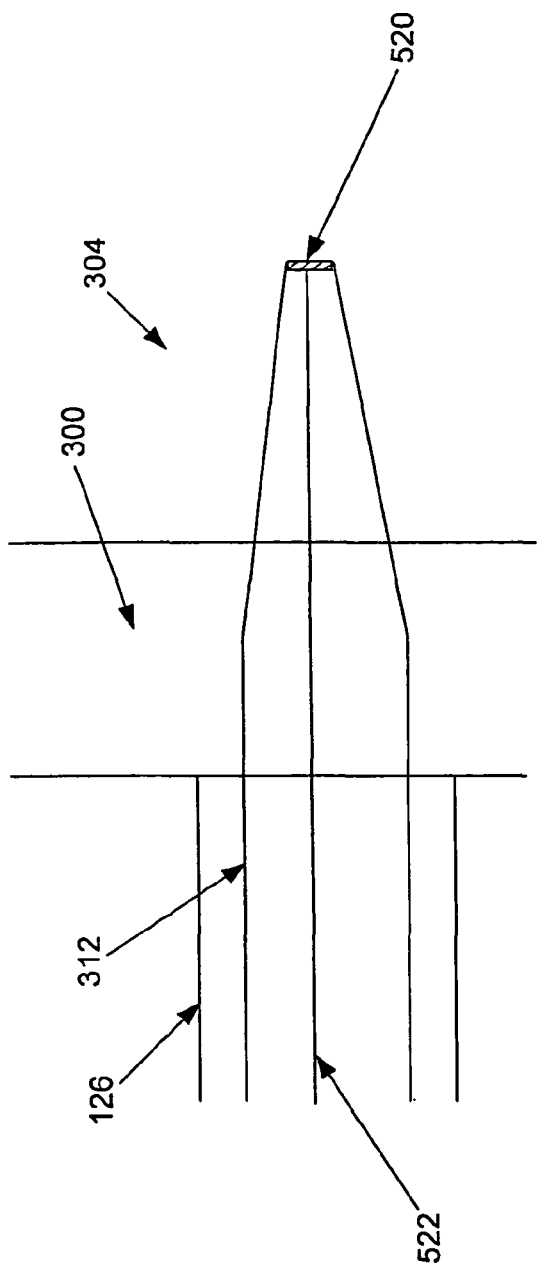
Figure 5L:
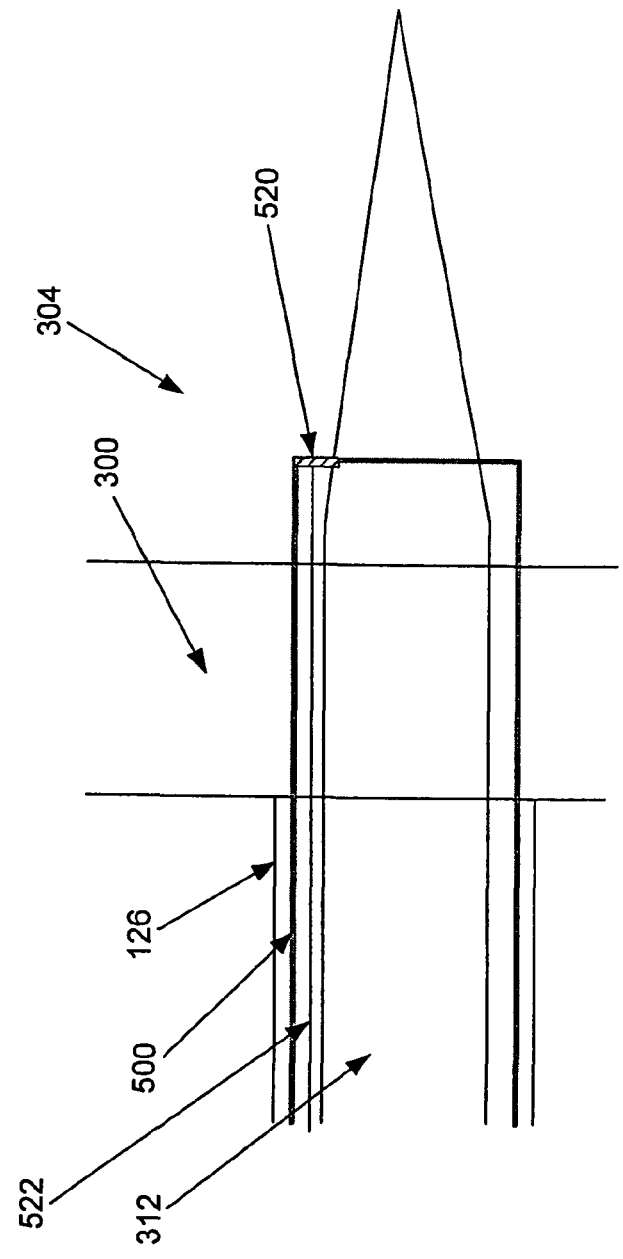

Referring to FIG. 5K, an embodiment of a traversing member is depicted with a flow sensor (520) disposed at the distal tip, in a configuration selected to access flows straight ahead of the advancing traversing member (312). FIG. 5L depicts a similar embodiment with a flow sensor coupled to a sleeve (500). In each embodiment, flow rate data is transmitted proximally, preferably via a sensor lead (522). Small flow rate sensors, based upon Doppler ultrasound or laser diode technology are well known in the art and available from suppliers such as Transonic Systems, Inc. of Ithaca, N.Y.

Referring to FIG. 5M, an embodiment of a traversing member is depicted with an echo time sensor (524) disposed at the distal tip, in a configuration selected to access flows straight ahead of the advancing traversing member (312). FIG. 5N depicts a similar embodiment with an echo time sensor (524) coupled to a sleeve (500). In each embodiment, echo time data is transmitted proximally, preferably via a sensor lead (526). An echo time sensor (524), generally comprising a radiation emitter and detector configured to detect the proximity of objects in a manner similar to that of sonar technology, may be interfaced with a computer-generated sound signal which changes frequency in accordance with changes in echo time. With such a configuration, for example, the sound frequency when the echo time sensor (524) is positioned within a relatively high-density tissue wall (300) may vary significantly from the sound frequency associated with a relatively low density, open cavity (304), thereby facilitating detection of the distal end of a traversing member (312) as it is advanced across the tissue wall (300) and into the adjacent open cavity (304).

Referring to FIG. 6A, an embodiment of a tissue wall traversal process in accordance with the present invention is summarized in flowchart format. Referring to FIG. 6A, a balloon structure is positioned adjacent a tissue wall (530). Inflation of the balloon optimizes visualization by providing a relatively unobstructed field of view (532). Subsequent to confirming an appropriate position upon the tissue wall or navigating to an appropriate position utilizing visualization feedback (534), the traversing member is advanced across the tissue wall while the position is monitored for confirmation of appropriate positioning (538). With the traversing member appropriately positioned across the tissue wall, the balloon is deflated and retracted proximally to leave the transecting member in place across the tissue wall (540).

Referring to FIG. 6B, another embodiment of a tissue wall traversal process in accordance with the present invention is summarized in flowchart format, the embodiment of FIG. 6B differing from that of FIG. 6A in that the embodiment of FIG. 6B comprises an additional step of flushing a volume entrapped between a concave balloon surface to provide better translucency for image capture, in a process wherein a structure similar to that described in reference to FIGS. 2 and 4 is utilized.

A process similar to that of FIG. 6A or 6B may be utilized, for example, in a transseptal crossing procedure wherein safe access to the left atrium of the heart is desired. Referring back to FIG. 3A, in such an embodiment, tissue structures 306 and 308 may represent portions of the wall of a right atrium cavity (302), the tissue wall (300) may represent the atrial septum, and the second cavity (304) may represent the left atrium of the heart. In accordance with the aforementioned techniques and structures, the collapsed catheter distal end (100) may be advanced toward the atrial septum, guided into position by wall (300) terrain (310) such as the outline of the fossa ovalis.

Appropriate positioning of the working lumen (124) relative to the outlines of the fossa ovalis may be confirmed utilizing images from the imaging element (108) with a preferably fully expanded (128) balloon (102) urged against the atrial septum, subsequent to which a traversing member (312), such as a Brockenbrough™ needle, may be advanced into the atrial septal wall through the working lumen (124), as observed through the tubular member (126), and preferably also through redundant visualization modalities, such as ultrasound and/or fluoroscopy. Further, the traversing member (312) may be instrumented with a sensor, such as a pressure, flow rate, color shade, or other sensor, to confirm that the distal tip of the traversing member (312) is indeed where the operator thinks it is.

Although the invention has been described herein with reference to specific embodiments, many modifications therein will readily occur to those of ordinary skill in the art without departing from the inventive concepts taught herein. Accordingly, all such variations and modifications are included within the intended scope of the invention as defined by the following claims.

The invention claimed is:

1. A method for traversing a tissue wall in a body, comprising:
   endoluminally advancing a direct visualization balloon catheter having an expandable balloon at a distal end and an imaging element into a first cavity opposite a tissue wall from a second cavity;
   approaching the tissue wall with said balloon catheter;
   adjusting the relative positioning between the distal end of the balloon catheter and the tissue wall based upon direct visualization feedback;
   engaging the tissue wall with a distal face of the expandable balloon, which allows a lumen of the balloon catheter to extend through the distal face of the expandable balloon and define a path to the tissue wall;
   controllably advancing a tissue traversing member out of the lumen of the balloon catheter, through the distal face of the expandable balloon, and through the tissue wall into the second cavity;
   upon traversing the tissue wall, confirming a position of the traversing member in the second cavity using an endoluminally advanced imaging element or sensing element positioned in the second cavity; and
   withdrawing the balloon catheter away from the tissue wall, while leaving the tissue traversing member positioned across the tissue wall and in the second cavity.

2. The method of claim 1, wherein approaching the tissue wall comprises
advancing the catheter distal end to a position adjacent the tissue wall with the catheter distal end in a contracted shape, and
expanding the catheter distal end into an expanded shape such that a distal face of the expandable balloon is substantially normal to the longitudinal axis of the balloon catheter to facilitate a larger direct visualization field of view of the tissue wall.

3. The method of claim 1, wherein adjusting the relative positioning comprises capturing images with an imaging element positioned within an interior of the catheter distal end, the images representing one or both of structures located immediately adjacent an exterior of the catheter distal end within a field of view of the imaging element, and structures comprising the catheter distal end within the field of view of the imaging element.

4. The method of claim 1, wherein engaging the tissue wall comprises advancing the catheter toward the tissue wall until contact is observed in the direct visualization feedback.

5. The method of claim 4, wherein engaging the tissue wall further comprises ejecting saline between the catheter distal end and the tissue wall to displace blood or other fluids in order to enhance visualization of the tissue wall.

6. The method of claim 1, wherein controllably advancing the tissue traversing member comprises observing a relative positioning of the tissue wall, the tissue traversing member, and the catheter distal end with direct visualization feedback.

7. The method of claim 1, wherein controllably advancing the tissue traversing member comprises monitoring a variable selected from a group consisting of pressure, color, oxygen saturation, flow rate, and echo timing, in order to determine the position of the tissue traversing member member relative to the tissue wall.

8. The method of claim 1, wherein the tissue wall is an atrial septum and approached from a right atrium, and wherein the tissue traversing member is controllably advanced through the atrial septum into a left atrium.

9. The method of claim 8, wherein adjusting the relative positioning comprises locating the position of a fossa ovalis upon the atrial septum.

10. A system to controllably traverse a tissue wall in a body, comprising:
an elongate tubular member having a distal end and defining a working lumen;
an inflatable balloon coupled to the distal end of the elongate tubular member, the balloon having a distal face and a proximal end, where, when expanded the distal face is substantially normal to the longitudinal axis of the working lumen;
a first imaging element disposed in an interior of the balloon;
a lighting element disposed in the interior of the balloon;
a tubular element defining a lumen between the distal end of the balloon and a distal end of the working lumen of the elongate tubular member;
a tissue traversing element configured to advance from a first cavity through and across a tissue wall into a second cavity, wherein the tissue traversing element is disposed within the working lumen of the elongate tubular member and positioned to slidably extend through the working lumen and tubular element lumen and beyond the balloon distal face within a field of view of the first imaging element; and
an endoluminally advanceable sensing element or second imaging element coupled to the tissue traversing member or to a sleeve surrounding the tissue traversing member and configured for detection in the second cavity to confirm a position of the traversing member or the sleeve in the second cavity.

11. The system of claim 10, wherein the elongate tubular member further defines at least one balloon sizing lumen to supply fluid to expand the balloon.

12. The system of claim 10, wherein the elongate tubular member further defines a lumen for transmitting light energy and image data between one or more external devices and the respective lighting and imaging elements.

13. The system of claim 10, wherein the first imaging element comprises a charge-coupled device.

14. The system of claim 10, wherein the first imaging element comprises an optical fiber.

15. The system of claim 10, wherein the lighting element comprises a structure selected from the group consisting of an incandescent light source, a light-emitting diode, and an optical fiber.

16. The system of claim 10, wherein the tissue traversing member carries the sensing element which is configured to monitor a variable selected from a group consisting of pressure, color, oxygen saturation, flow rate, and echo timing.

17. The system of claim 10, wherein the first imaging element is disposed adjacent the balloon proximal end.

18. The system of claim 10, wherein the first imaging element is disposed adjacent the balloon distal end.

19. The system of claim 18, wherein a field of view of the first imaging element does not include portions of the balloon.

20. The system of claim 18 wherein the distal end of the balloon forms a concave surface out of which a field of view of the first imaging element extends distally.

21. The method of claim 1, where the traversing member further includes a piercing tip and a traversing lumen, where the traversing lumen provide access across the tissue wall after withdrawing the balloon catheter away from the tissue wall.

22. The method of claim 21, further comprising advancing tools through the traversing lumen.

23. The method of claim 1, wherein endoluminally advancing a direct visualization balloon catheter comprises intravascularly advancing a direct visualization balloon catheter.

* * * * *

UNITED STATES PATENT AND TRADEMARK OFFICE
CERTIFICATE OF CORRECTION

| | | |
|---|---|---|
| PATENT NO. | : 8,172,747 B2 | |
| APPLICATION NO. | : 10/949032 | |
| DATED | : May 8, 2012 | |
| INVENTOR(S) | : Daniel T. Wallace et al. | |

It is certified that error appears in the above-identified patent and that said Letters Patent is hereby corrected as shown below:

On the first page, under (75) Inventors, after Frederic H. Moll, Woodside, CA (US), please add --Gregory J. Stahler, San Jose, CA (US)-- and In claim 7, column 9, line 36, please delete the duplicate word "member"

Signed and Sealed this
Seventeenth Day of July, 2012

David J. Kappos
*Director of the United States Patent and Trademark Office*